(12) United States Patent
Campbell et al.

(10) Patent No.: US 10,173,038 B2
(45) Date of Patent: Jan. 8, 2019

(54) RETRACTABLE SHEATH DEVICES, SYSTEMS, AND METHODS

(71) Applicant: W. L. Gore & Associates, Inc., Newark, DE (US)

(72) Inventors: Carey V. Campbell, Flagstaff, AZ (US); Robert L. Cleek, Flagstaff, AZ (US); Edward H. Cully, Flagstaff, AZ (US); Peter Heicksen, Flagstaff, AZ (US); Theresa A. Holland, Flagstaff, AZ (US); Thane L. Kranzler, Flagstaff, AZ (US); Mei Li, Flagstaff, AZ (US); Bruce M. Steinhaus, Flagstaff, AZ (US); Benjamin M. Trapp, Flagstaff, AZ (US); Thomas G. Triebes, Flagstaff, AZ (US); Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 461 days.

(21) Appl. No.: 14/018,053

(22) Filed: Sep. 4, 2013

(65) Prior Publication Data

US 2014/0066897 A1 Mar. 6, 2014

Related U.S. Application Data

(60) Provisional application No. 61/789,949, filed on Mar. 15, 2013, provisional application No. 61/697,269, filed on Sep. 5, 2012.

(51) Int. Cl.
*A61M 25/10* (2013.01)
*A61L 29/08* (2006.01)
(Continued)

(52) U.S. Cl.
CPC .......... *A61M 25/10* (2013.01); *A61L 29/041* (2013.01); *A61L 29/085* (2013.01); *A61L 29/146* (2013.01);
(Continued)

(58) Field of Classification Search
CPC ................ A61M 25/10; A61M 31/00; A61M 2025/1081; A61M 2025/105; A61M 2025/0057
See application file for complete search history.

(56) References Cited

U.S. PATENT DOCUMENTS 4,193,138 A    3/1980  Okita
4,902,423 A *  2/1990  Bacino ............... 210/500.36
(Continued)

FOREIGN PATENT DOCUMENTS

CN    101437467 A    5/2009
CN    101795630      8/2010
(Continued)

OTHER PUBLICATIONS

Salzmann, et al. Effects of balloon dilatation on ePTFE structural characteristics. J Biomed Mater Res Sep. 15, 1997; 36(4) :498-507.
(Continued)

*Primary Examiner* — Scott Medway

(57) ABSTRACT

The invention is directed to delivery medical devices that enable consistent "on-demand" delivery of therapeutic agents to a vessel. The medical device of the current invention comprises retractable sheath comprising neckable elements. The medical device of the current invention comprises an expandable member, a hydrophilic coating comprising at least one therapeutic agent about the expandable member or structural layer and a retractable outer sheath with a selectively permeable microstructure. The design and methods disclosed herein ensures that therapeutic agent
(Continued)

delivery occurs essentially only during retraction of the outer sheath, minimizing coating and/or therapeutic agent loss to the bloodstream and providing controlled delivery to the treatment site.

22 Claims, 16 Drawing Sheets

(51) Int. Cl.
    *A61L 29/14*     (2006.01)
    *A61L 29/16*     (2006.01)
    *A61L 29/04*     (2006.01)
    *A61F 2/962*     (2013.01)
    *A61F 2/958*     (2013.01)

(52) U.S. Cl.
    CPC .............. *A61L 29/16* (2013.01); *A61F 2/962* (2013.01); *A61F 2002/9583* (2013.01); *A61M 2025/105* (2013.01); *A61M 2025/1081* (2013.01); *A61M 2025/1086* (2013.01)

(56) References Cited

U.S. PATENT DOCUMENTS

| | | | |
|---|---|---|---|
| 4,994,072 A * | 2/1991 | Bhate et al. | 606/194 |
| 5,049,275 A * | 9/1991 | Gillberg-LaForce et al. | 210/500.27 |
| 5,066,298 A | 11/1991 | Hess | |
| 5,074,871 A * | 12/1991 | Groshong | 606/170 |
| 5,091,205 A * | 2/1992 | Fan | 427/2.28 |
| 5,211,654 A | 5/1993 | Kaltenbach | |
| 5,213,576 A | 5/1993 | Abiuso et al. | |
| 5,232,444 A | 8/1993 | Just et al. | |
| 5,269,755 A | 12/1993 | Bodicky | |
| 5,304,121 A * | 4/1994 | Sahatjian | 604/509 |
| 5,318,531 A | 6/1994 | Leone | |
| 5,458,568 A | 10/1995 | Racchini et al. | |
| 5,476,589 A * | 12/1995 | Bacino | 210/500.36 |
| 5,478,349 A | 12/1995 | Nicholas | |
| 5,571,086 A * | 11/1996 | Kaplan et al. | 604/96.01 |
| 5,599,306 A * | 2/1997 | Klein et al. | 604/103.01 |
| 5,609,629 A | 3/1997 | Fearnot et al. | |
| 5,616,119 A | 4/1997 | Davis | |
| 5,693,014 A * | 12/1997 | Abele et al. | 604/103.08 |
| 5,773,019 A | 6/1998 | Ashton et al. | |
| 5,868,704 A | 2/1999 | Campbell et al. | |
| 5,893,840 A | 4/1999 | Hull et al. | |
| 5,902,745 A | 5/1999 | Butler et al. | |
| 5,954,706 A | 9/1999 | Sahatjian | |
| 5,964,730 A | 10/1999 | Williams et al. | |
| 6,001,386 A | 12/1999 | Ashton et al. | |
| 6,096,070 A | 8/2000 | Ragheb et al. | |
| 6,149,641 A | 11/2000 | Ungs | |
| 6,280,411 B1 | 8/2001 | Lennox | |
| 6,306,166 B1 | 10/2001 | Barry et al. | |
| 6,364,856 B1 * | 4/2002 | Ding et al. | 604/103.02 |
| 6,395,208 B1 | 5/2002 | Herweck et al. | |
| 6,447,540 B1 * | 9/2002 | Fontaine et al. | 623/1.12 |
| 6,450,989 B2 * | 9/2002 | Dubrul et al. | 604/104 |
| 6,524,274 B1 | 2/2003 | Rosenthal et al. | |
| 6,544,222 B1 | 4/2003 | Yang | |
| 6,716,444 B1 | 4/2004 | Castro | |
| 6,733,474 B2 | 5/2004 | Kusleika | |
| 6,753,071 B1 | 6/2004 | Pacetti | |
| 6,939,320 B2 | 9/2005 | Lennox | |
| 6,939,374 B2 | 9/2005 | Banik et al. | |
| 6,955,661 B1 | 10/2005 | Herweck et al. | |
| 7,020,529 B2 | 3/2006 | Krall et al. | |
| 7,066,904 B2 | 6/2006 | Rosenthal et al. | |
| 7,179,251 B2 | 2/2007 | Palasis | |
| 7,572,245 B2 | 8/2009 | Herweck et al. | |
| 7,637,886 B2 | 12/2009 | Herweck et al. | |
| 7,713,573 B2 * | 5/2010 | Owens et al. | 427/2.1 |
| 7,740,793 B2 | 6/2010 | Herweck et al. | |
| 7,811,622 B2 | 10/2010 | Bates et al. | |
| 7,871,659 B2 * | 1/2011 | Cook et al. | 427/2.1 |
| 7,875,284 B2 | 1/2011 | Reyes et al. | |
| 7,892,201 B1 | 2/2011 | Laguna et al. | |
| 7,919,108 B2 | 4/2011 | Reyes et al. | |
| 7,947,015 B2 | 5/2011 | Herweck et al. | |
| 8,048,440 B2 * | 11/2011 | Chang et al. | 424/423 |
| 8,048,503 B2 * | 11/2011 | Farnsworth et al. | 428/36.4 |
| 8,062,270 B2 * | 11/2011 | Sweeney | 604/264 |
| 8,114,049 B2 | 2/2012 | Freyman et al. | |
| 8,162,880 B2 | 4/2012 | Jayaraman | |
| 8,177,743 B2 | 5/2012 | Lennox | |
| 8,398,703 B2 * | 3/2013 | Kassab et al. | 623/1.15 |
| 2002/0077693 A1 * | 6/2002 | Barclay et al. | 623/1.13 |
| 2003/0028210 A1 | 2/2003 | Boyle et al. | |
| 2004/0230316 A1 * | 11/2004 | Cioanta et al. | 623/23.66 |
| 2004/0247640 A1 * | 12/2004 | Zhao et al. | 424/423 |
| 2005/0085841 A1 * | 4/2005 | Eversull et al. | 606/190 |
| 2005/0182361 A1 | 8/2005 | Lennox | |
| 2006/0190022 A1 | 8/2006 | Beyar et al. | |
| 2006/0253072 A1 * | 11/2006 | Pai et al. | 604/104 |
| 2008/0015500 A1 | 1/2008 | Herweck et al. | |
| 2008/0021385 A1 | 1/2008 | Barry et al. | |
| 2008/0033476 A1 * | 2/2008 | Greene | 606/194 |
| 2008/0118544 A1 | 5/2008 | Wang | |
| 2008/0140002 A1 * | 6/2008 | Ramzipoor et al. | 604/103.02 |
| 2008/0213463 A1 | 9/2008 | Cook et al. | |
| 2009/0076448 A1 * | 3/2009 | Consigny et al. | 604/103.01 |
| 2009/0226502 A1 | 9/2009 | Chen | |
| 2009/0227948 A1 | 9/2009 | Chen et al. | |
| 2009/0227949 A1 | 9/2009 | Knapp et al. | |
| 2009/0264975 A1 * | 10/2009 | Flanagan et al. | 623/1.2 |
| 2009/0287182 A1 | 11/2009 | Bishop et al. | |
| 2010/0021519 A1 | 1/2010 | Shenoy | |
| 2010/0042199 A1 | 2/2010 | Burton | |
| 2010/0049225 A1 | 2/2010 | To et al. | |
| 2010/0209472 A1 * | 8/2010 | Wang | 424/423 |
| 2010/0228333 A1 * | 9/2010 | Drasler et al. | 623/1.11 |
| 2011/0015725 A1 | 1/2011 | Bates et al. | |
| 2011/0054396 A1 | 3/2011 | Kangas et al. | |
| 2011/0137244 A1 * | 6/2011 | Lee | A61L 31/10 604/103.02 |
| 2011/0190863 A1 | 8/2011 | Ostroot et al. | |
| 2011/0196340 A1 | 8/2011 | Barry et al. | |
| 2011/0251582 A1 | 10/2011 | Lennox | |
| 2011/0270226 A1 | 11/2011 | Kocur et al. | |
| 2011/0301565 A1 | 12/2011 | Weber | |
| 2012/0035283 A9 * | 2/2012 | Xu et al. | 521/50.5 |
| 2012/0053517 A1 | 3/2012 | Chen et al. | |
| 2012/0283820 A1 * | 11/2012 | Tseng et al. | 623/1.23 |
| 2013/0103062 A1 | 4/2013 | To et al. | |
| 2013/0158675 A1 * | 6/2013 | Hutchins, III | A61M 25/0017 623/23.66 |
| 2013/0226131 A1 | 8/2013 | Bacino et al. | |
| 2013/0253426 A1 * | 9/2013 | Campbell et al. | 604/103.02 |

FOREIGN PATENT DOCUMENTS

| | | |
|---|---|---|
| EP | 0565604 | 7/1999 |
| EP | 0708671 | 11/2001 |
| EP | 0747069 | 9/2002 |
| EP | 0863729 | 12/2004 |
| EP | 0920843 | 2/2005 |
| EP | 1263492 | 4/2005 |
| EP | 0836429 | 11/2005 |
| EP | 1148899 | 4/2006 |
| EP | 1351739 | 5/2006 |
| EP | 1800702 | 6/2007 |
| EP | 1011743 | 7/2011 |
| EP | 2043704 | 8/2011 |
| WO | 96/40305 | 12/1996 |
| WO | 01/64278 | 9/2001 |
| WO | 03/015677 | 2/2003 |
| WO | 2008/064058 | 5/2008 |
| WO | WO-2009/051614 A1 | 4/2009 |
| WO | WO-2009/111712 A1 | 9/2009 |

(56) References Cited

FOREIGN PATENT DOCUMENTS

| WO | WO-2009111716 A1 | 9/2009 |
| WO | 2010/093800 | 8/2010 |
| WO | 2013/074185 | 5/2013 |

OTHER PUBLICATIONS

International Search Report for PCT/US2013/058171 dated Dec. 16, 2013, corresponding to U.S. Appl. No. 14/018,053, 4 pages.
International Search Report for PCT/US2013/058242 dated Dec. 19, 2013, corresponding to U.S. Appl. No. 14/018,202, 4 pages.

* cited by examiner

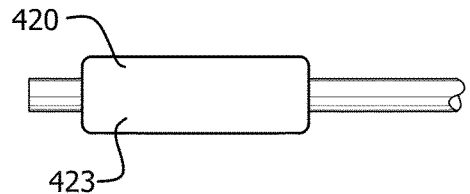
FIG. 4E
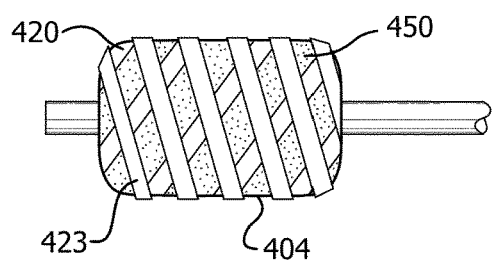
FIG. 4F
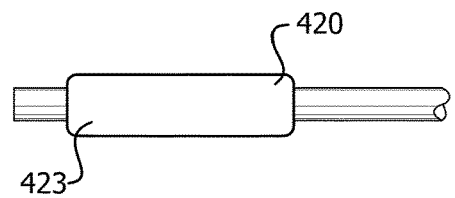
FIG. 4G
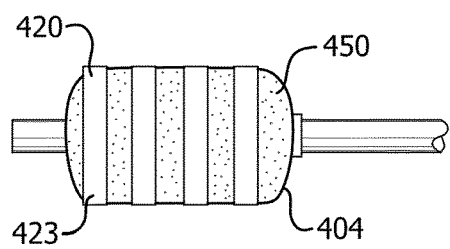
FIG. 4H
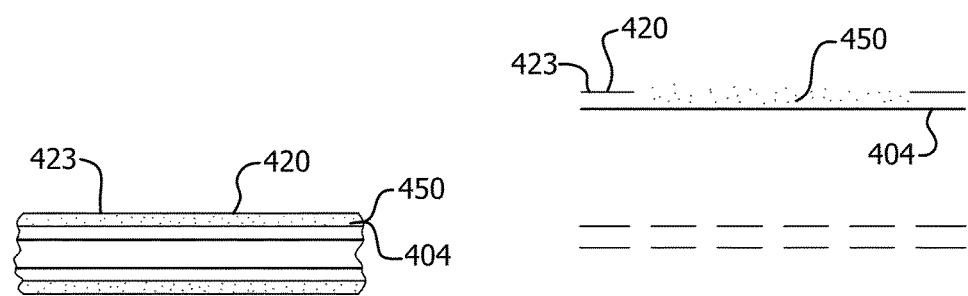
FIG. 4I
FIG. 4J

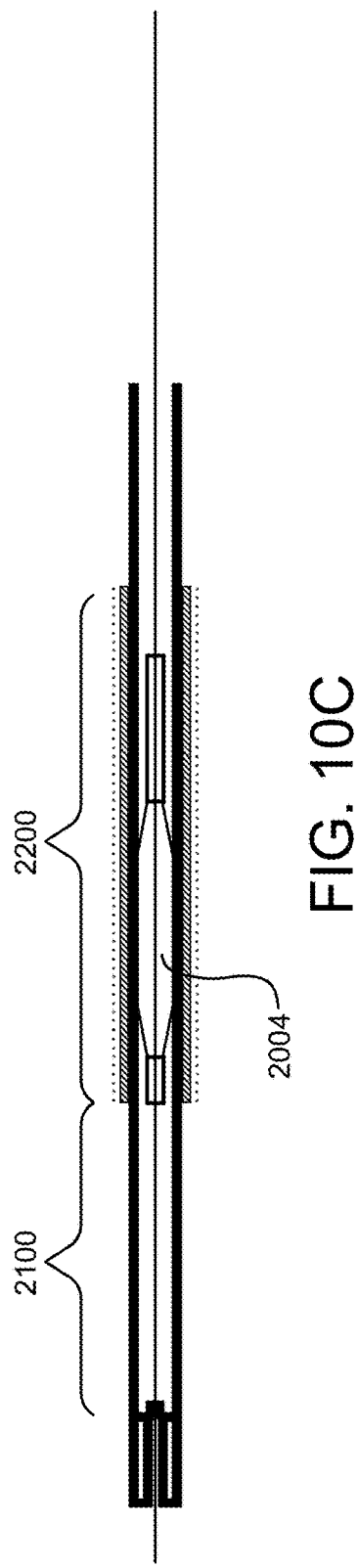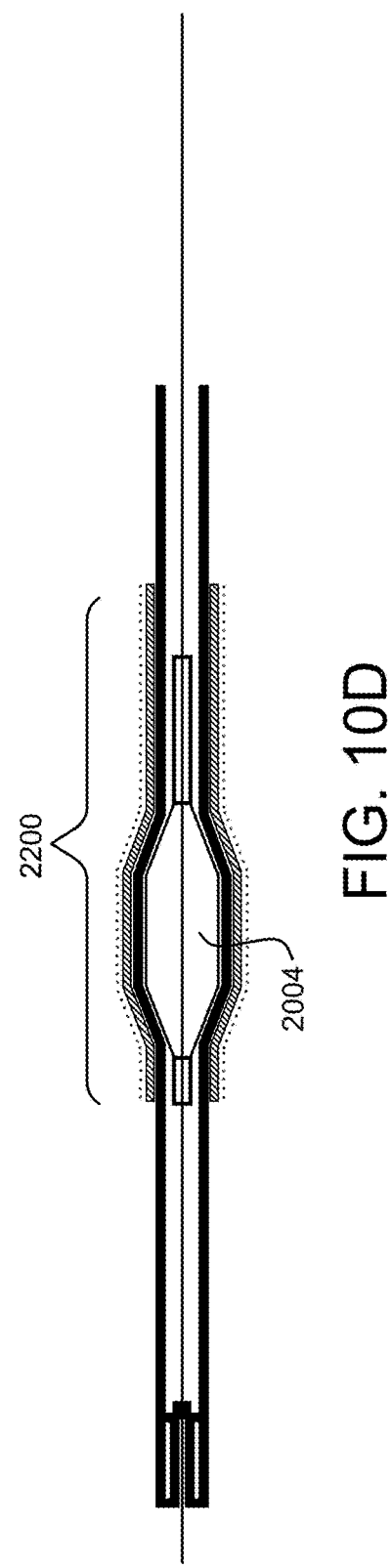

RETRACTABLE SHEATH DEVICES, SYSTEMS, AND METHODS

BACKGROUND

The systemic administration of therapeutic agents treats the body as a whole even though the disease to be treated may be localized. In some cases of localized disease, systemic administration may not be desirable because the drug agents may have unwanted effects on parts of the body which are not to be treated or because treatment of the diseased part of the body requires a high concentration of a drug agent that may not be achievable by systemic administration.

It is therefore often desirable to administer therapeutic agents to only localized sites within the body. Common examples of where this is needed include cases of localized disease (e.g., coronary heart disease) and occlusions, lesions, or other disease in body lumens. Several devices and methods for localized drug delivery are known. In one example, such devices are drug delivery balloons, and methods of their use include the steps of coating a balloon attached to a balloon catheter with a drug and a carrier matrix, inserting the catheter into a blood vessel, tracking the balloon to a desired location, and expanding the balloon against the surrounding tissue to transfer the drug locally at the intended treatment site.

One of the potential drawbacks to localized drug delivery is the possibility of premature or unintended release of the drug, the carrier matrix, and/or the drug/carrier matrix combination. This may occur during tracking and placement at the treatment site of a drug delivery device and post delivery as the device is withdrawn from the body. Such unintended release may result from drug diffusion, device contact with areas proximate the treatment site, or washing of the drug from the surface of the delivery device due to blood flow. This is of particular concern when the device comprises a therapeutic agent of a type or dosage not intended to be released to tissue or blood outside the treatment site.

Drugs or coating components shed in this unwanted fashion may be in particulate form or may be in solution. The downstream release of undesirable particles is known as "particulation". For example, particulation of large particles can create problems such as ischemia in tissues, especially in tissues supplied by small diameter vessels. Furthermore, the resulting effects of biodistribution of such particles are not well understood and may result in adverse effects.

When combining a drug with an implantable device, the drug may be in a solid form (as a particulate or crystal) but is preferably released from the device as a solubilized molecule (or as a nonsoluble particle of known size in a solubulized matrix). The advantages of localized, solubilized drug delivery are believed to be uniform drug distribution at the treatment site, well-known drug biodistribution, and the avoidance of particulation.

In view of the potential drawbacks to current, localized drug delivery, there exists a need for devices and methods that allow for controlled, localized delivery of drug agents, especially soluble or hydrated agents, to specific treatment sites within a mammalian body that avoids premature or unintended drug release away from the intended treatment site, while ensuring that desired dosing occurs.

SUMMARY

The present disclosure is directed to an expandable medical device that has a retractable, outer sheath that enables localized, on-demand delivery of a therapeutic agent to a vessel or other lumen of cavity, while not substantially delivering or releasing said therapeutic agent as the device is being tracked to or positioned at the desired treatment site. The medical device of the current invention comprises an expandable member with or without a structural layer serving as a substrate over said expandable member, at least one coating comprising at least one therapeutic agent on the expandable member or structural layer, and an outer sheath comprising a selectively permeable microstructure. During use, the underlying hydrophilic coating becomes hydrated or partially hydrated and can facilitate fluid transfer across the outer sheath. However, in such instances, said outer sheath's microstructure limits unwanted, premature release of said therapeutic agent. Stated differently, said outer sheath's microstructure limits particulation of said therapeutic agent during tracking. Upon expansion, the outer sheath disposed over the expandable member or structural layer retracts, exposing the underlying hydrated, or partially hydrated coating. Retraction can be actuated in a variety of ways, both passively and actively. Once the hydrated or partially hydrated hydrophilic coating is exposed, the therapeutic agent is delivered to the treatment site. In an embodiment, said expandable member is a medical balloon.

The present disclosure is also directed to a medical device comprising retractable outer sheath having at least one neckable element forming said sheath. Neckable elements can be selectively permeable or substantially impermeable in order to limit undesired release of a therapeutic agent and/or prevent particulation during tracking.

In an embodiment, the invention comprises a medical device comprising an expandable member and a selectively permeable retracting sheath disposed around said expandable member. Said sheath can comprise one or more "neckable" elements. Said elements cover the expandable member at a first state, for example, in an un- or partially-inflated state. As the sheath is expanded or further expanded, said elements become strained and assume a second state, decreasing in width and increasing in overall length. The transition from first toward second state serves to open or move the sheath and uncover the underlying expandable member. Said sheath can comprise at least one helically wrapped, neckable element; at least two adjacent annular, neckable elements; or at least two longitudinal, neckable elements. In an embodiment, the sheath is comprised of a netting or weave of neckable filaments where the interstitial spaces open upon stretching. In an embodiment, the width of said sheath element decreases upon expansion of an expandable member. In another embodiment, the length of said sheath element increases upon expansion of an expandable member. In an embodiment, said medical device further comprises a coating having a therapeutic agent. In an embodiment, said coating can be located between the sheath and the expandable member. In one embodiment, upon expansion, said coating is transferred to tissue in a hydrated or partially hydrated state. In another embodiment, said coating comprises a hydrophilic component. In another embodiment, said coating comprises a hydrophilic agent. In an embodiment, the therapeutic agent is the hydrophilic agent. In another embodiment, said coating comprises at least one compound selected from the group consisting of benzethonium chloride, poloxamer-188, polyethylene glycol, calcium salicylate, and hydroxypropyl-β-cyclodextrin. In another embodiment, said therapeutic agent is a hydrophobic agent. In another embodiment, said therapeutic agent comprises paclitaxel. In another embodiment, the retracting sheath can comprise a permeable microstructure that prevents or limits unintended transfer of a coating and/or a therapeutic agent through said sheath prior to expandable member expanding. In a further embodiment, said coating and therapeutic agent are disposed between the surface of the expandable member and the sheath and when said expandable member expands, said sheath allows rapid transfer of said coating and therapeutic agent through the sheath to an area external to said sheath. In one embodiment, said expandable member is a medical balloon. In another embodiment, said medical device comprises a catheter. In another embodiment, said sheath undergoes microscopic or macroscopic wetting while said balloon and sheath are in the unexpanded state and being tracked to a desired location within a vessel. In another embodiment, said sheath is modified to include a hydrophilic component located within at least a part of the sheath and/or on part or all of said sheath's external surface. In another embodiment, said hydrophilic component of said sheath wets facilitating microscopic wetting in a vessel. In another embodiment, the outer sheath is wet-out by a prescribed preparatory procedure prior to being inserted into the patient. In another embodiment, said sheath comprises a fluoropolymer. In another embodiment, said neckable elements comprises a microstructure comprised of nodes interconnected by fibrils. In another embodiment, said nodes are aligned substantially parallel to the length (or longer dimensional) axis of said neckable element and said fibrils are aligned at an angle which is not substantially parallel to said axis. In another embodiment, said nodes are aligned at an angle which is not substantially parallel to the length (or longer dimensional) axis of said neckable element and said fibrils are aligned substantially parallel to said axis. In another embodiment, the distance between said fibrils increases as said outer sheath expands. In another embodiment, the distance between said nodes increases as said outer sheath expands. In another embodiment, the orientation, size, or conformation of said nodes and/or fibrils changes as said outer sheath expands. In another embodiment, the microstructure of the neckable element changes as said expandable member expands. In another embodiment, said sheath comprises an expanded polymer, such as expanded polytetrafluoroethylene (ePTFE). In another embodiment, said expandable member further comprises a structural layer. In another embodiment, said structural layer comprises said coating and therapeutic agent. In constructing the above embodiment, a coating can be applied to the outer surface of the neckable elements which make up the sheath. Once applied, the sheath can be everted so that the outer surface becomes the inner surface and is disposed about the expandable member.

In another embodiment, a medical device can comprise a retracting sheath which covers an underlying surface and can comprise neckable elements, wherein when said expandable member and sheath are expanded, said neckable elements neck and said underlying surface is exposed. Said elements cover the expandable member at a first state, for example, in an un- or partially-inflated state. As the sheath is expanded or further expanded, said elements become strained and assume a second state, decreasing in width and increasing in overall length. The transition from first toward second state serves to open or move the sheath and uncover the underlying surface. Said sheath can comprise at least one helically wrapped, neckable element; at least two adjacent annular, neckable elements; or at least two longitudinal, neckable elements. In an embodiment, the width of said sheath element decreases upon expansion of an expandable member. In another embodiment, the length of said sheath element increases upon expansion of an expandable member. In an embodiment, said medical device further comprises a coating having a therapeutic agent. In an embodiment, said coating can be on the underlying surface. In one embodiment, upon expansion, said coating is transferred to tissue.

Another embodiment of the invention comprises a balloon catheter comprising a balloon comprising a coating and a therapeutic agent disposed around the outer surface of said balloon, and a retracting sheath disposed around said balloon. Said sheath can comprise at least one neckable element. Said elements cover the expandable member at a first state, for example, in an un- or partially-inflated state. As the sheath is expanded or further expanded, said elements become strained and assume a second state, decreasing in width and increasing in overall length. The transition from first toward second state serves to open or move the sheath and uncover the underlying balloon. In an embodiment, said balloon comprises a coating. Said sheath can comprise at least one helically wrapped, neckable element, at least two adjacent annular, neckable elements, or at least two longitudinal, neckable elements. In an embodiment, the width of said sheath element decreases upon expansion of the balloon. In another embodiment, the length of said sheath element increases upon expansion of balloon. In an embodiment, a coating comprising a therapeutic agent can be located between the sheath and the balloon. In one embodiment, upon expansion said coating is transferred to tissue in a hydrated or partially hydrated state. In another embodiment, said coating comprises a hydrophilic component. In another embodiment, said coating comprises a hydrophilic agent. In an embodiment, the therapeutic agent is the hydrophilic agent. In another embodiment, said coating comprises at least one compound selected from the group consisting of benzethonium chloride, poloxamer-188, polyethylene glycol, calcium salicylate, and hydroxypropyl-β-cyclodextrin. In another embodiment, said therapeutic agent is a hydrophobic agent. In another embodiment, said therapeutic agent comprises paclitaxel. In another embodiment, the retracting sheath can comprise a permeable microstructure that prevents or limits unintended transfer of therapeutic agent through said sheath but permits the influx of fluid. In one embodiment, said expandable member is a medical balloon. In another embodiment, said medical device comprises a catheter. In another embodiment, said sheath undergoes microscopic wetting while said balloon and sheath are in the unexpanded state and being tracked to a desired location within a vessel. In another embodiment, said sheath is modified to include a hydrophilic component located within at least a part of the sheath and/or on part or all of said sheath's external surface. In another embodiment, said hydrophilic component of said sheath wets facilitating microscopic wetting in a vessel. In another embodiment, the outer sheath is wet-out by a prescribed preparatory procedure prior to being inserted into the patient. In another embodiment, said sheath comprises a fluoropolymer. In another embodiment, said sheath comprises a microstructure comprised of nodes interconnected by fibrils. In another embodiment, said sheath comprises an expanded polymer, such as expanded polytetrafluoroethylene (ePTFE). In another embodiment, said expandable member further comprises a structural layer. In another embodiment, said structural layer comprises said coating and therapeutic agent. In constructing the above embodiment, a coating can be applied to the outer surface of the neckable elements which make up the sheath. Once applied, the sheath can be everted so that the outer surface becomes the inner surface and is disposed about the balloon.

Another embodiment of the invention comprises a balloon catheter comprising: a balloon comprising a coating and a therapeutic agent disposed around the outer surface of said balloon; a first outer sheath disposed around said coating; and a second outer sheath disposed around said first outer sheath, wherein said second sheath does not prevent macroscopic wetting of said sheath in an unexpanded state, wherein said first sheath has a microstructure with characteristics which prevent macroscopic wetting of said sheath in the unexpanded state and when said balloon and sheaths are expanded, said first sheath forms openings which expose sections of the underlying coating and allows rapid transfer of said coating to a surrounding area. In an embodiment, said first sheath comprises neckable elements. In an embodiment, said first sheath is configured to split or tear to form openings. In another embodiment, said first sheath can be folded or otherwise configured onto the balloon in such a way that a plurality of openings are not exposed through the thickness of said first sheath until expanded. In one embodiment, said coating is transferred through said second sheath and onto or into a target tissue. In one embodiment, upon expansion said coating is transferred in a hydrated or partially hydrated state. In another embodiment, said coating remains substantially adhered to the target tissue for greater than 1 minute after contact between balloon and treatment site is substantially eliminated. In another embodiment, said sheaths undergo microscopic wetting in a vessel while said balloon and sheaths are in the unexpanded state and being delivered to a desired location within a vessel. In an embodiment, said transfer of the hydrated or partially hydrated coatings is facilitated when said second sheath is in contact with a vessel wall. In another embodiment, said first sheath has a microstructure composed of nodes and fibrils. In an embodiment said first sheath comprises a fluoropolymer. In an embodiment said first sheath comprises ePTFE. In another embodiment, said second sheath has a microstructure composed of nodes and fibrils. In another embodiment said second sheath comprises a fluoropolymer. In an embodiment said second sheath comprises ePTFE. In another embodiment, said nodes are aligned longitudinally to the longitudinal axis of said balloon catheter and said fibrils are aligned circumferentially to said axis. In another embodiment, said nodes are aligned circumferentially to the longitudinal axis of said balloon catheter and said fibrils are aligned longitudinally to said axis. In another embodiment, said coating comprises a hydrophilic component. In another embodiment, said therapeutic agent is a hydrophilic agent. In another embodiment, said therapeutic agent is a hydrophobic agent. In another embodiment, said therapeutic agent is paclitaxel. In another embodiment, said balloon further comprises a structural layer. In another embodiment, said structural layer comprises said coating and therapeutic agent.

In another embodiment, the invention comprises a medical device comprising: an expandable member; an outer sheath disposed around said expandable member comprising a splittable, tubular casing, and a coating contained inside said splittable casing comprising a therapeutic agent. Said splittable casing has walls which can comprise a selectively permeable microstructure that limits or prevents the unintended transfer of said therapeutic agent through said casing walls when expandable member is in an unexpanded state. Upon expansion of the underlying expandable member, the splittable casing opens to expose the lumen to the surrounding tissue. In an embodiment, said casing has a microstructure composed of nodes interconnected by fibrils. In another embodiment, said casing comprises a fluoropolymer. In another embodiment, said casing comprises an expanded polymer such as ePTFE. In another embodiment, said nodes are aligned substantially parallel to the length (or longer dimensional) axis of said splittable casing and said fibrils are aligned at an angle which is not substantially parallel to said axis. In another embodiment, said nodes are aligned at an angle which is not substantially parallel to the length (or longer dimensional) axis of said casing and said fibrils are aligned substantially parallel to said axis. In another embodiment, said coating comprises a hydrophilic component. In another embodiment, said coating comprises a hydrophilic agent. In an embodiment, the therapeutic agent is the hydrophilic agent. In another embodiment, said coating comprises at least one compound selected from the group consisting of benzethonium chloride, poloxamer-188, polyethylene glycol, sodium salicylate, and hydroxypropyl-β-cyclodextrin. In another embodiment, said therapeutic agent is a hydrophobic agent. In another embodiment, said therapeutic agent is paclitaxel. In one embodiment, upon expansion said coating is transferred in a hydrated or partially hydrated state. In another embodiment, said coating remains substantially adhered to the target tissue for greater than 1 minute after contact between expandable member and treatment site is substantially eliminated. In an embodiment, said casing has characteristics which allow macroscopic wetting of said casing in the unexpanded state and at least partial hydration of the coating. In another embodiment, said casing undergoes only microscopic wetting in a vessel while said expandable member and sheath are in the unexpanded state and being tracked to a desired location within a vessel. In another embodiment, said casing is modified to include a hydrophilic component located within at least a part of the casing wall and/or on part or all of said casing's external surface. In another embodiment, said hydrophilic component of said casing facilitates microscopic wetting of the casing (serving as the sheath) before and as said sheath is expanded. In another embodiment, fluid external to said casing is allowed to flow through the external wall(s) of said casing and contact said therapeutic agent before and as said sheath is expanded in a vessel. In another embodiment, the casing is wet-out by a prescribed preparatory procedure prior to being inserted into the patient. In another embodiment, the coating also wets the casing when said casing is expanded. In an embodiment, said casing can be helically wrapped around the expandable member. In other embodiment, said casing can comprise an annular ring disposed about the expandable member. In an embodiment, a casing can be longitudinally oriented. In another embodiment, a plurality of said casings can be disposed about the expandable member. In another embodiment, said casing comprises a tearable seam along its length. In another embodiment, said casing comprises a tearable seam around, or angled around its circumference. Said seam comprises a structurally weakened area, e.g., perforations, a thinning in the wall thickness, or the like. In another embodiment, the splittable casing can comprise a permeable microstructure that prevents or limits unintended transfer of therapeutic agent through said casing. In one embodiment, upon expansion, the coating is transferred to said tissue in a hydrated or partially hydrated state. In another embodiment, the casing becomes strained as said expandable member expands facilitating splitting of the casing. In an embodiment, the splitting of the casing during expansion facilitates release of the hydrated or partially hydrated coating from inside the casing. In one embodiment, said expandable member is a medical balloon. In another embodiment, said medical device comprises a catheter. In another embodiment, the splittable casing can comprise an impermeable microstructure that prevents or limits unintended transfer of therapeutic agent through said casing.

In another embodiment, the invention comprises a medical device comprising: an expandable member; an outer sheath disposed around said expandable member comprising a tubular, neckable casing, and a coating contained inside said casing comprising a therapeutic agent as well as second coating comprising a second therapeutic agent located on a surface underlying the outer sheath. Said neckable casing has walls which can comprise a permeable microstructure that initially limits unintended transfer of said therapeutic agent through said casing walls when said casing has a substantially closed microstructure; wherein said coating is disposed inside the casing; and wherein when said expandable member and neckable casing (serving as the sheath) are expanded, said casing walls develop a more open microstructure which allows the transfer of said therapeutic agent to an area external to said sheath. In addition, upon expansion, said neckable casing necks to at least partially expose the underlying second coating, which also allows the transfer of second therapeutic agent to an are external said sheath. In various embodiments, the casing walls can prevent transfer of particles out of said casing greater than about 25 microns in size. For example, the maximum effective pore size of the microstructure at second diameter is less than or equal to about 25 microns. In other embodiments, particles greater than about 25 microns in size can transfer through said casing walls. In an embodiment, said casing has a microstructure composed of nodes interconnected by fibrils. In another embodiment, said casing comprises a fluoropolymer. In another embodiment, said casing comprises an expanded polymer such as ePTFE. In another embodiment, said nodes are aligned substantially parallel to the length (or longer dimensional) axis of said casing and said fibrils are aligned at an angle which is not substantially parallel to said axis. In another embodiment, said nodes are aligned at an angle which is not substantially parallel to the length (or longer dimensional) axis of said casing and said fibrils are aligned substantially parallel to said axis. In another embodiment, the distance between said fibrils increases as said outer sheath, comprising the casing, expands. In another embodiment, the distance between said fibrils increases as said outer sheath, comprising the casing, expands. In another embodiment, the distance between said nodes increases as said outer sheath expands. In another embodiment, the orientation, size, or conformation of said nodes and/or fibrils changes as said outer sheath expands. In a further embodiment, a second coating can be located in between the expandable member and the neckable casing. In another embodiment both of said coatings comprise a therapeutic agent, which can be the same or different. In another embodiment, one or both of said coatings comprise a hydrophilic component. In another embodiment, one or both of said coatings comprises a hydrophilic agent. In an embodiment, the therapeutic agent is the hydrophilic agent. In another embodiment, one or both of said coatings comprises at least one compound selected from the group consisting of benzethonium chloride, poloxamer-188, polyethylene glycol, sodium salicylate, and hydroxypropyl-β-cyclodextrin. In another embodiment, said therapeutic agent is a hydrophobic agent. In another embodiment, said therapeutic agent is paclitaxel. In one embodiment, said coating is transferred through said casing and onto or into a target tissue. In one embodiment, upon expansion said coating is transferred through said casing in a hydrated or partially hydrated state. In another embodiment, said coating remains substantially adhered to the target tissue for greater than 1 minute after contact between expandable member and treatment site is substantially eliminated. In another embodiment, the casing becomes strained as said expandable member expands facilitating transfer of the hydrated or partially hydrated coating through the casing. In an embodiment, said casing has characteristics which prevent macroscopic wetting of said casing in the unexpanded state, wherein said coating and therapeutic agent are disposed inside the casing, and wherein when said expandable member is expanded, substantially all of said casing wets out rapidly and allows rapid transfer of said coating through the casing. In another embodiment, said coating also wets the casing when said casing is expanded. In another embodiment, said sheath comprising a casing allows rapid transfer of said coating and therapeutic agent because said sheath rapidly wets out just prior to and/or during expansion. In another embodiment, said casing undergoes only microscopic wetting in a vessel while said balloon and sheath are in the unexpanded state and being tracked to a desired location within a vessel. In another embodiment, bodily fluids substantially wet-out the casing when said sheath is expanded. In another embodiment, said casing is modified to include a hydrophilic component located within at least a part of the casing wall and/or on part or all of said casing's external surface. In another embodiment, said hydrophilic component of said casing facilitates microscopic wetting of the casing (serving as the sheath) before and as said sheath is expanded. In another embodiment, substantially all of said sheath is wetted by the time said sheath is fully expanded (i.e., expanded to its rated or nominal diameter). In another embodiment, fluid external to said casing is allowed to flow through the external wall(s) of said casing and contact said therapeutic agent before and as said sheath is expanded in a vessel. In another embodiment, said wetting of the casing is facilitated when said sheath is in contact with the vessel wall. In another embodiment, the casing is wet-out by a prescribed preparatory procedure prior to being inserted into the patient. In another embodiment, both coatings also wet the casing when said casing is expanded. In an embodiment, said casing can be helically wrapped around the expandable member. In other embodiment, said casing can comprise an annular ring disposed about the expandable member. In an embodiment, a casing can be longitudinally oriented. In another embodiment, a plurality of said casings can be disposed around the expandable member. In another embodiment, upon expansion of the expandable member said casing necks and exposes said second coating which is transferred onto or into a target tissue. In one embodiment, upon expansion both coatings are transferred to said tissue in a hydrated or partially hydrated state. In one embodiment, upon expansion and necking of the casing(s), said second coating is transferred in a hydrated or partially hydrated state. In another embodiment, said second coating remains substantially adhered to the target tissue for greater than 1 minute after contact between expandable member and treatment site is substantially eliminated. In another embodiment, the casing becomes strained as said expandable member expands facilitating necking of the casing. In an embodiment, the necking of the casing during expansion facilitates driving out of the hydrated or partially hydrated coating through the casing wall. In one embodiment, said expandable member is a medical balloon. In another embodiment, said expandable member further comprises a structural layer. In another embodiment, said structural layer comprises said coating and therapeutic agent. In another embodiment, said medical device comprises a catheter.

In another embodiment, the neckable casing can comprise an impermeable microstructure that prevents or limits unintended transfer of therapeutic agent through said casing.

Other embodiments of the invention comprise a method of delivering a therapeutic agent to a desired location within a vessel comprising, inserting a catheter in a vessel, said catheter comprising an expandable member comprising a coating with a therapeutic agent, a sheath disposed around said expandable member, wherein said sheath has a selectively permeable microstructure that prevents said coating from being transported through substantially all of said sheath but allows said coating to be at least partially hydrated, and wherein said coating and therapeutic agent are disposed between the surface of the expandable member and the sheath, advancing said catheter to a desired location within said vessel, and expanding the expandable member at the desired location within said vessel, and wherein said sheath retracts and exposes a hydrated or partially hydrated coating and therapeutic agent from between the surface of the expandable member and the sheath to an area external to said sheath when said sheath is in an unexpanded state. In one embodiment, said sheath comprises at least one neckable element. In one embodiment, said expandable member is a medical balloon. In another embodiment, said sheath comprises a fluoropolymer. In another embodiment, the sheath comprises a microstructure comprised of nodes interconnected by fibrils. In another embodiment, said nodes are aligned longitudinally to the longitudinal axis of said balloon catheter and said fibrils are aligned circumferentially to said axis. In another embodiment, said nodes are aligned circumferentially to the longitudinal axis of said balloon catheter and said fibrils are aligned longitudinally to said axis. In another embodiment, said nodes expand (elongate) said outer sheath expands. In another embodiment, said nodes are spread apart as said outer sheath expands. In another embodiment, the orientation of said nodes changes as said outer sheath expands. In another embodiment, said fibrils are spread apart as said outer sheath expands. In another embodiment, said fibrils are unfolded, straightened out or reoriented as said outer sheath expands. In another embodiment, said nodes are aligned substantially parallel to the length (or longer dimensional) axis of said neckable element and said fibrils are aligned at an angle which is not substantially parallel to said axis. In another embodiment, said nodes are aligned at an angle which is not substantially parallel to the length (or longer dimensional) axis of said neckable element and said fibrils are aligned substantially parallel to said axis. In another embodiment, said sheath comprises ePTFE. In another embodiment, said therapeutic agent is a hydrophilic agent. In another embodiment, said therapeutic agent is a hydrophobic agent. In another embodiment, said therapeutic agent is paclitaxel. In another embodiment, said coating is hydrophilic. In another embodiment, said expandable member further comprises a structural layer. In another embodiment, said structural layer comprises said coating and therapeutic agent. In another embodiment, the hydrated or partially hydrated hydrophilic coating containing a therapeutic agent is tissue adherent, and thus, even after the expandable member is removed from the site, the drug continues to be absorbed into the tissue until the coating and drug dissipate from the site. This approach effectively increases the total drug delivery time to the tissue.

In another embodiment of the invention, said coating contains a hydrophobic drug that is complexed or sequestered by one or more solubilizing agents. In another embodiment, said solubilizing agent helps said hydrophobic drug transfer to a target tissue. In another embodiment, said solubilizing agent, when delivered to the intended tissue site, dissociates from said drug and the drug binds to tissue.

Another embodiment of the invention comprises a balloon catheter comprising a balloon comprising a relatively low-solubility therapeutic agent in the form of micelles, liposomes, micro-aggregates, nanospheres, microspheres, nanoparticles, microparticles, crystallites, or inclusion complexes combined with or suspended in a coating material which hydrates or dissolves more rapidly than the agent, the agent and coating being disposed around the outer surface of said balloon, a sheath disposed around said balloon, wherein said coating and therapeutic agent are disposed between the surface of the balloon and the sheath, and wherein when said sheath is wetted, said coating hydrates and the form of said agent remain essentially intact and wherein when said balloon and sheath are expanded and the sheath is retracted, transfer of the hydrated coating and agent occurs onto or into a target tissue.

Another embodiment of the invention comprises a sheath disposed around a coating disposed about an expandable member wherein the sheath is purposefully modified with a wetting agent to facilitate wetting of said sheath. However, said modified sheath, even when wet-out, limits drug transfer across said sheath.

In another embodiment, an expandable device such as a stent or stent-graft may be mounted to the "on-demand" agent delivery construct of the invention, delivered to a site within the body where the expandable device is expanded and placed using the construct of the invention. The advantage of this application is that a therapeutic can be delivered to a treatment site along with another treatment device.

In another embodiment, following therapeutic treatment with the "on-demand" agent delivery construct of the invention, an expandable device such as a stent, stent-graft, or other endoprosthesis may be placed in the treatment region, and the construct of the invention is used to "touch-up" or otherwise modify the degree to which at least a portion of the device is expanded.

In another embodiment, placement and/or "touching up" of an endoprosthesis with therapeutic agent delivery constructs of the instant invention may comprise transferring a therapeutic agent from the construct to the endoprosthesis (e.g., by absorptive transfer), whereby the endoprosthesis subsequently becomes a drug delivery endoprosthesis which operates therapeutically over short or long periods of time.

BRIEF DESCRIPTION OF THE DRAWINGS

The exemplary embodiments of the present invention will be described in conjunction with the accompanying drawings. The accompanying drawings are included to provide a further understanding of the invention and are incorporated in and constitute a part of this specification, illustrate embodiments of the invention and together with the description serve to explain the principles of the invention. Figures are not drawn to scale.

FIGS. 10A through 10D depict the procedural steps for one method of use employing the embodiment shown in FIGS. 9A to 9B.

DETAILED DESCRIPTION OF THE EMBODIMENTS

Certain embodiments of the present disclosure are directed to a wettable or selectively permeable sheath that can permit at least partial hydration of an underlying therapeutic agent while preventing the release of said therapeutic agent in an unexpanded state. Other embodiments of the present disclosure are directed to retractable sheaths which are constructed of neckable elements that reduce in diameter as the element is elongated, thereby exposing an underlying surface. These embodiments can be utilized with agent delivery constructs, such as a catheter comprising an agent delivery construct for transfer of at least one therapeutic agent to a desired site within a mammalian body. The therapeutic agent delivery construct of the instant invention comprises additional structures which ensure drug delivery to the target site without significant drug loss during device tracking to the target site. In one embodiment, said agent delivery construct comprises an expandable member. In another embodiment, said expandable member is a medical balloon. (As used herein balloon and medical balloon are used interchangeably, unless otherwise noted).

For clarity, the figures, the description and the examples describe and depict an agent delivery construct comprising a medical balloon. However, the invention is not intentioned to be limited to this one embodiment. As described below, other expandable members comprising retracting or "shrinking" sheaths are envisioned as part of this invention.

Reference will now be made in detail to embodiments of the present invention, examples of which are illustrated in the accompanying drawings.

Figure 1A:
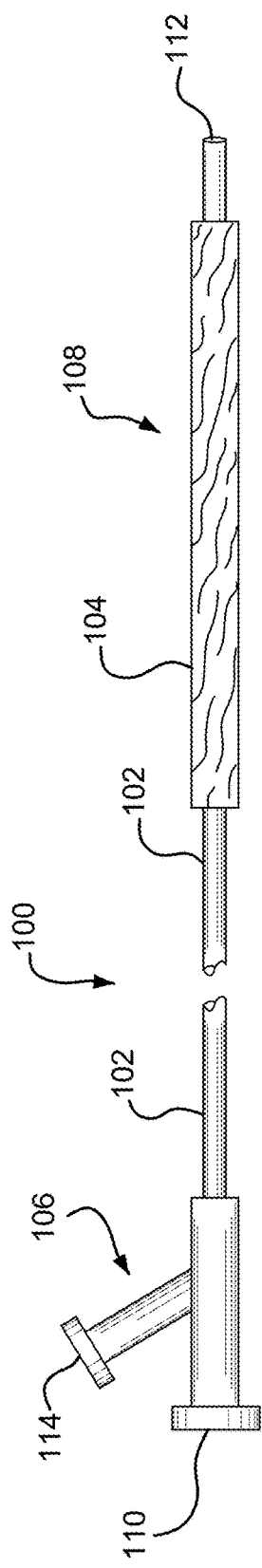
FIG. 1A depicts a side view of a general balloon catheter having an elongated tubular body with a balloon in a first, unexpanded state.

FIG. 1A is illustrative of a balloon catheter 100 having an elongated tubular body 102 with a balloon 104. In one embodiment balloon 104 may be a length adjustable balloon.

The elongated tubular body 102 has a proximal control end 106 and a distal functional end 108. The balloon catheter also has a proximal guidewire lumen 110 that extends through the length of the elongated tubular body 102 and exits the distal end at a guidewire port 112. The balloon catheter shown is an "Over The Wire" configuration, as commonly known in the art. Alternatively, the catheter could have a guidewire port located midway between proximal and distal ends and therefore have a "Rapid Exchange" configuration, as commonly known in the art. The balloon catheter 100 also incorporates a proximal inflation port 114 that allows fluid communication between the inflation port 114 and the lumen of the balloon 104. The length and inner and outer diameter of the tubular body are selected based upon the desired application of the medical device. The tubular body generally has a circular cross-sectional configuration. However, oval and other cross-sectional configurations can also be used. In one embodiment, said balloon catheter is compatible with 0.038", 0.035", 0.018" or 0.014", 0.010", or similar conventional guidewires.

The tubular body must have sufficient structural integrity to permit the medical device to be advanced to distal vascular locations without bending or buckling upon insertion. Various techniques are known for manufacturing the tubular bodies. In one embodiment, the tubular body is manufactured by extrusion of a biocompatible polymer.

The invention is also directed to an expandable medical device that delivers a therapeutic agent to a vascular site using consistent "on-demand" delivery while not substantially delivery or releasing therapeutic agent(s) while the device is being tracked to a desired location within the vasculature. The medical device of the current invention comprises an expandable member with (or without) a structural or substrate layer over the expandable member, at least one hydrophilic coating comprising at least one therapeutic agent disposed on the expandable member or structural layer, and an outer sheath comprising a selectively permeable microstructure disposed about the coating. During use, the underlying hydrophilic coating becomes hydrated or partially hydrated and facilitates fluid transfer across the outer sheath. However, said outer sheath's microstructure in the unexpanded state prevents unwanted, premature release of said therapeutic agent.

Upon expansion, the outer sheath can be configured to retract or otherwise expose the underlying layer. As the underlying layer is exposed, at least a portion of the coating is exposed and delivered to the treatment site. In one embodiment, the hydrated or partially hydrated coating comprises a therapeutic agent, and once the outer sheath retracts, the therapeutic agent transfers to the surrounding tissue. In another embodiment, said expandable member is a medical balloon.

Figure 1B:
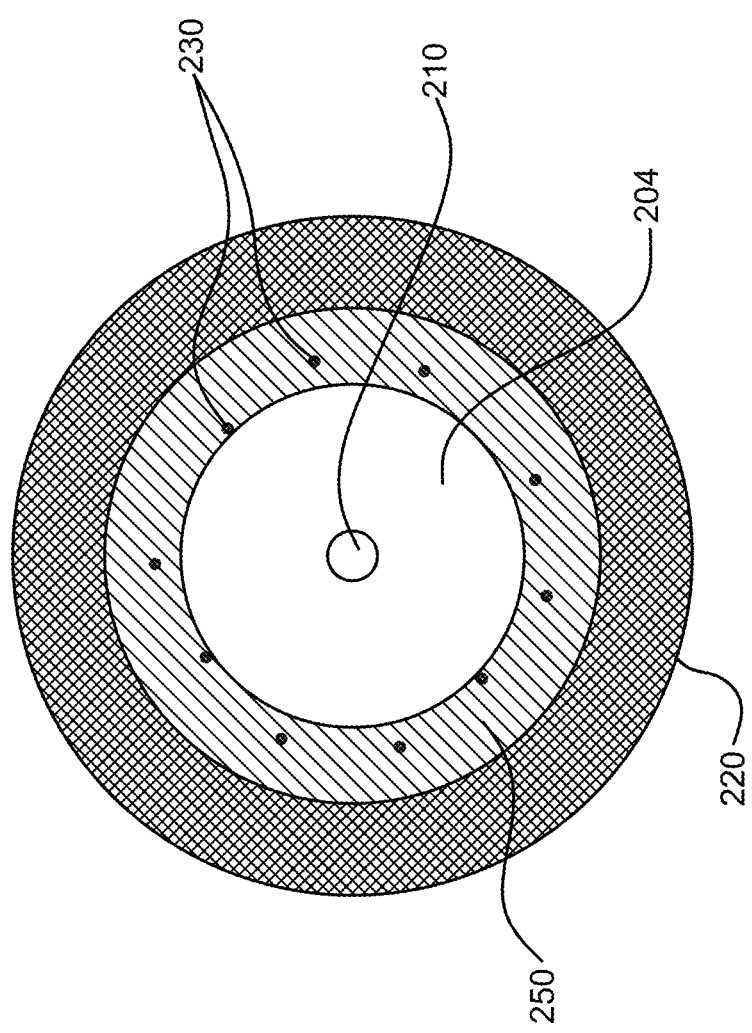
FIG. 1B depict a cross-section of the drug delivery balloon of the invention in its first, unexpanded state.

The agent delivery construct of the invention comprises several aspects to help control delivery of therapeutic agents from an expandable member. FIG. 1B is a cross-section of an agent delivery construct comprising a balloon in its first, uninflated, state. The construct comprises a balloon 204, a hydrophilic coating 250 on balloon 204 and an outer sheath 220. Hydrophilic coating 250 further comprises at least one therapeutic agent 230. Also depicted is guidewire lumen 210 that extends through the length of the balloon. In one embodiment, said hydrophilic coating is substantially dehydrated prior to device insertion into the vasculature. In another embodiment, the outer sheath 220 is made from a material having a permeable microstructure. In another embodiment, outer sheath 220 is wrapped or folded over hydrophilic coating 250 at a first, uninflated diameter.

Upon retraction, the coating 250 is at least partially exposed to the surrounding environment. It will be understood that the coating 250 may, in some embodiments, be hydrophilic. In another embodiment, upon expansion of the balloon 204 and retraction of the sheath 220, the hydrophilic coating 250 migrates to the surrounding environment in a hydrated or partially hydrated state. In another embodiment, outer sheath 220 is wetted before expansion to allow hydration or partial hydration of the hydrophilic coating 250. In another embodiment, said sheath is at least partially wetted before expansion. In another embodiment, coating 250 is tissue adherent and remains adhered to the target tissue even after the device is removed. This embodiment allows for continued drug transfer from the adherent coating at the tissue interface until the tissue adherent coating dissipates from the target tissue, as described in the co-pending and co-assigned U.S. Patent Publication 2010/0233266. In another embodiment, the coating comprises a thixotropic gel.

Materials which may exhibit permeable microstructures are known to the art. These include, but are not limited to, fibrillated structures, such as expanded fluoropolymers (for example, expanded polytetrafluoroethylene (ePTFE)) or expanded polyethylene (as described in U.S. Pat. No. 6,743,388 and incorporated herein by reference); fibrous structures (such as woven or braided fabrics; non-woven mats of fibers, microfibers, or nanofibers; materials made from processes such as electrospinning or flash spinning; polymer materials consisting of melt or solution processable materials such as fluoropolymers, polyamides, polyurethanes, polyolefins, polyesters, polyglycolic acid (PGA), polylactic acid (PLA), and trimethylene carbonate (TMC), and the like; films with openings created during processing (such as laser- or mechanically-drilled holes); open cell foams; microporous membranes made from materials such as fluoropolymers, polyamides, polyurethanes, polyolefins, polyesters, PGA, PLA, TMC, and the like; porous polyglycolide-co-trimethylene carbonate (PGA:TMC) materials (as described in U.S. Pat. No. 8,048,503 and incorporated herein by reference); or combinations of the above. Processing of the above materials may be used to modulate, enhance or control permeability. Such processing may help close the microstructure (thus lower permeability) or help open the microstructure, or a combination of both. Such processing which may help close the microstructure may include, but is not limited to: calendaring, coating (discontinuously or continuously), compaction, densification, coalescing, thermal cycling, or retraction and the like. Such processing that may help open the microstructure may include, but is not limited to: expansion, perforation, slitting, patterned densification and/or coating, and the like. In another embodiment, said materials comprise micropores between nodes interconnected by fibrils, such as in ePTFE. In another embodiment, said material comprises micropores in an essentially nodeless ePTFE, as described in U.S. Pat. No. 5,476,589, which is hereby incorporated by reference in its entirety for all purposes.

In another embodiment of the invention, the surface(s) or outward configuration of the sheath material may be modified with textures, protrusions, spikes, wires, blades, scorers, depressions, grooves, coatings, particles, and the like. In another embodiment of the invention, the surface(s) or outward configuration of the sheath material may be modified with needles, cannulae, and the like. These modifications may serve various purposes such as to modify tissues into which therapeutic agents will be (or have been) delivered, control placement of the system of the invention, and direct fluid transfer. Such textures may help in increased transfer of a therapeutic agent onto, more deeply and/or into deeper tissues. Optionally, coatings can aid in microscopic or macroscopic wetting of said sheath material. In one embodiment, said coating of said sheath material comprises crosslinked polyvinyl alcohol (see, e.g., U.S. Pat. No. 7,871,659). In another embodiment, said coating of said permeable microstructure material comprises a heparin coating, such those described in U.S. Pat. Nos. 4,810,784 and 6,559,131, both of which are hereby incorporated by reference herein in their entireties for all purposes.

In another embodiment of the invention, the location(s) of the permeable microstructure may be varied. For example, a sheath may be constructed such that only a portion of its microstructure is permeable. Such a configuration may be desirable where fluid transfer is not desired to occur, for example, at one or both of the ends of the expandable medical device of the invention. This may be desirable where multiple drug delivery devices will be used in a specific anatomy, and it would be undesirable to overlap treatments sites, i.e., delivering too much drug to a particular site.

In another embodiment, the sheath may contain or be marked with radiopaque markers or be constructed to be radiopaque in its entirety. Such radiopaque indicators are used by clinicians to properly track and place an expandable medical device of the invention.

As used herein, the term "permeable microstructure" refers to a structure or material that permits inflow of a fluid but limits or restricts outflow of a hydrated or at least partially hydrated coating, when in an unexpanded state. One skilled in the art will appreciate various testing methods which characterize the permeability. These methods include, but are not limited to, characterizations of air or liquid flux across the microstructure at a given pressure differential, characterization which determines the pressure differential at which different fluids strike through the microstructure such as Water Entry Pressure or Bubble Point, characterization of porosity, and visual characterization such as inter-nodal or inter-fibril spacing as measured from an image (e.g. from a scanning electron microscope or light microscope).

As used herein, the terms "micropores" and "microporous" refer to openings in materials, for example the area between ePTFE nodes and fibrils. Usually, as in the case of ePTFE, these micropores contain air when the material is not "wetted".

As used herein, the terms "wet", "wet-out" and "wetted" refer to the displacement of air in a microporous material by a fluid. Wetting of a material lowers the resistance to subsequent fluid transfer and facilitates the flow of fluids though the microporous material. Furthermore, these microporous materials are intended to be open cell structures, meaning the micropores are interconnected, and not closed cell structures. This allows fluid to flow through the material. Capillary effects may also play an important role in fluid flow though the material as wetting occurs, especially for highly porous materials with small interconnected pores. The microstructure of outer sheath can be selected to maximize capillary effects to produce improved hydration. Wetting can be accomplished with the aid of one or more surfactants added to the fluid. The surfactant can absorb onto the fluid-vapor, solid-fluid, and solid-vapor interfaces, which in turn modifies the wetting behavior of hydrophobic materials. The wetting will also depend on the viscosity to the fluid.

As used herein, the term "coating" refers to one or more materials disposed on the surface of a substrate. In the present disclosure, the substrate may include the structural layer or substrate or expandable member or outer sheath. Said coating may lie completely on the surface or may be incorporated, in whole or in part, within the openings or pores present in a substrate. The latter coating configuration is commonly referred to in the art as "imbibed" or "filled" materials.

As used herein, the term "dry coating" or "dehydrated coating" refers to the inability of the coating alone to sufficiently wet the outer sheath by the displacement of air in a microporous material. Some dry coating embodiments may be formulated with at least one component that is in a liquid state in its pure form capable of causing wet-out, but when combined with additional components results in a dry coating. In contrast, as used herein, the term "pre-hydrated" refers to a coating that is hydrated or partially solvated prior to introduction into a body. Pre-hydrated coatings may not require wetting of the sheath.

As used herein, the term "vessel" refers to any luminal or tubular structure within the body to which these constructs can be utilized. This includes, but not limited to, vascular blood vessels, vascular defects such as arteriovenous malformations, aneurysm, or others, vessels of the lymphatic system, esophagus, intestinal anatomy, sinuous cavity, uterus, or other. The embodiments of the present invention are also suitable for the treatment of a malignant disease (i.e. cancer) within or associated with a vessel As used herein, the term "to neck" or "neckable" refers to the act of or ability to reduce in transverse dimension, e.g., a width, cross-section or diameter, when being elongated in a longitudinal dimension. With respect to certain embodiments described herein, upon expansion of an expandable member, neckable elements are elongated which cause a reduction in a transverse dimension, e.g., its width, cross-section or diameter, thereby exposing an underlying surface or layer.

As used herein, the term "to retract" or "retractable" refers to the act or ability of withdrawing, moving, or not increasing in surface area during expansion of an underlying expandable member or increasing to a lesser extent than the underlying member, thereby causing an underlying layer or surface, e.g., a coating and/or the surface of the expandable member and/or a structural layer, to be exposed to the surrounding environment. As described herein, in various embodiments, "to retract" or retractable" can refer to the act or ability of necking, tearing, breaking, or otherwise separating to expose an underlying layer or surface.

Figure 1C:
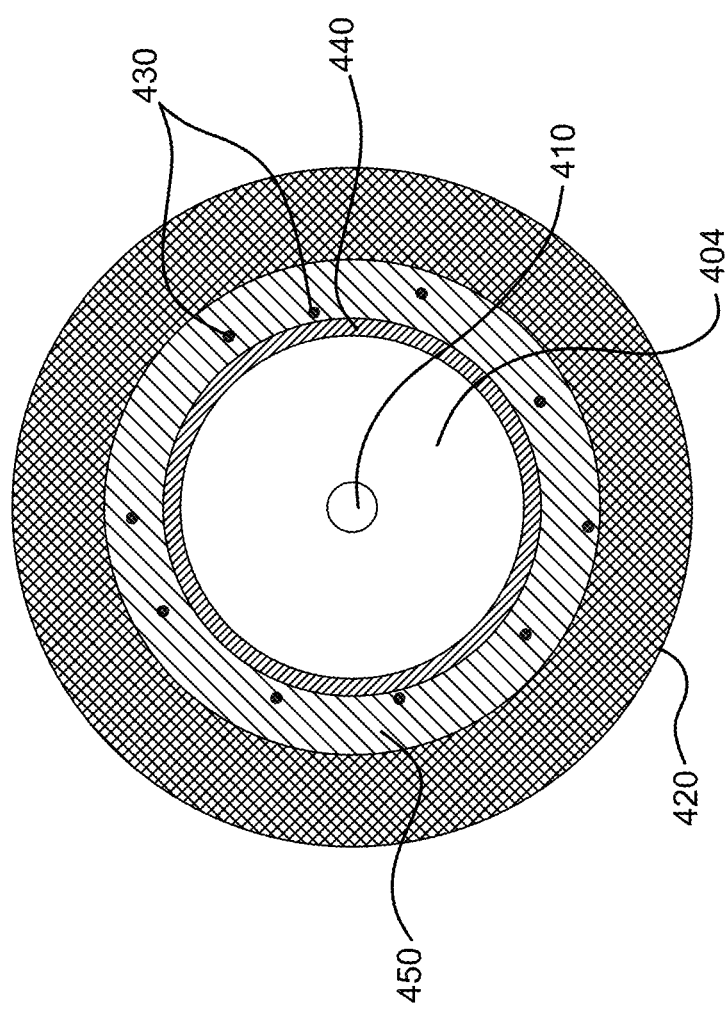
FIG. 1C depict a cross-section of the drug delivery balloon of the invention in its first, unexpanded state having a structural layer.

Another embodiment of the invention, as depicted in FIG. 1C, comprises a cross-section of an agent delivery construct in its first, unexpanded, state. In this embodiment, the construct comprises a balloon 404, a substrate or structural layer or cover 440, a hydrophilic coating 450 on balloon 104 and an outer sheath 420. Hydrophilic coating 450 further comprises at least one therapeutic agent 430. Also depicted is guidewire lumen 410 that extends through the length of the balloon. Structural layer 440 can serve many functions. One of its functions may be to serve as a substrate for uniformly applying the hydrophilic coating 450 to the underlying balloon 404. Since some balloon materials may not be conducive to being uniformly coated, the structural layer can serve as a scaffold to achieve a uniform coating. In addition, if the structural layer comprises an elastomer, the structural layer can help with recompaction of the underlying balloon (see, e.g., U.S. Pat. No. 6,120,477, Campbell, et al., which is hereby incorporated by reference in its entirety for all purposes). In another embodiment, the structural layer can be coated with said hydrophilic coating and said therapeutic agent prior to placement on an expandable member. With such a pre-fabricated, coating construct, any balloon can be converted to an agent delivery construct of the invention. Thus, one embodiment of the invention comprises using a coated structural layer and placing it on any "off the shelf balloon" or OEM balloon to make the balloon a drug delivery balloon. In another embodiment, the hydrophilic coating is coated onto structural layer 140 and then dehydrated or partially dehydrated. In another embodiment, said dehydrated or partially dehydrated hydrophilic coating comprises at least one therapeutic agent. In another embodiment, structural layer 140 and/or outer sheath 120 are wrapped or folded over at a first, uninflated diameter.

A structural layer, for example one made according to the examples below, also provides for a uniform tube to be coated at first state which will concentrically/uniformly expand up to a second state. In contrast, conventional Percutaneous Transluminal Angioplasty (PTA) balloons must be coated at second state (in their molded shape) and then be compacted down to a first state. A structural layer can be coated separate from the catheter or balloon on a mandrel, and later assembled onto the balloon with increased manufacturing yields, lower costs, and higher uniformity. As described above, the coating on said structural layer will be covered by an outer sheath. Either upon delivery to the target location at a first diameter, or as the balloon is inflated to its second state, the coating will become hydrated or partially hydrated.

The structural layer can be made from any material that is compatible with the coating and which can be expanded to accommodate expansion of the balloon. These materials include, but are not limited to ePTFE, fluoropolymers, expanded polyethylene, polyvinylchloride, polyurethane, silicone, polyethylene, polypropylene, polyurethane, polyglycolic acid, polyesters, polyamides, elastomers and their mixtures, blends and copolymers, are all suitable. In one embodiment, said structural layer comprises ePTFE. In another embodiment, said ePTFE is imbibed with an elastomer, such as a thermoplastic copolymer of tetrafluoroethylene and perfluoroalkylvinylether, which can be free of cross-linking monomers and curing agents as described in U.S. Pat. No. 8,048,440, hereby incorporated by reference in its entirety.

In another embodiment of the invention, the surface(s) or outward configuration of the structural layer (or expandable member if a structural layer is not used) may be modified with textures, folds, flaps, invaginations, corrugations, pleats protrusions, spikes, scorers, depressions, grooves, pores, coatings, particles, and the like or combinations thereof. In another embodiment, said depressions, grooves, and/or pores can be used increase the effective surface area over which the coating can be placed. Such surfaces can be etched to increase the effective surface area. In other embodiments, structural layer can comprise a fibrillated microstructure. The fibrils can comprise folds/micropleats to increase the effective surface area. This may help enhance the solvation or hydration cycle. It can also help in reduction of length or profile of the overall medical device. In another embodiment, the structural layer may comprise a wicking material. Wicking material can facilitate the hydration of the coating. As microwetting occurs wicking material can distribute the fluid. In further embodiments, the wicking material can be partially exposed, i.e., not covered by the outer sheath, at one or more sites along the medical device. The exposed sites allow for body fluids to migrate into wicking material and hydrate the coating. In an embodiment, the wicking layer can comprise a material having an open pore membrane of PTFE such as that described in U.S. Pat. No. 5,814,405 by Branca et al. entitled "Strong, Air Permeable Membranes of Polytetrafluoroethylene," which is hereby incorporated by reference describes in further detail. Other suitable materials can include open cell polyurethane foam, open cell silicone foam, open cell fluoropolymers, or any other pliable materials comprising micro or macro channels to allow infusion. Wicking material can contain a wetting agent as described herein to improve the distribution of the fluid. Wicking material can also serve as a sponge that holds the therapeutic agent until sufficient pressure between a body surface and the expandable member expels the therapeutic agent from the wicking material to the surrounding body surface.

In another embodiment of the invention and as an alternative to coating a structural layer which is subsequently combined with an expandable member, the coating material may itself be formed into a structural component that is combined with an expandable member. Such constructs eliminate the requirement for a structural layer per se, yet fully preserve the key functions provided by the coatings of the invention. Such constructs may also improve manufacturability and can be combined with most any expandable member, such as a balloon. For example, where the expandable member comprises a balloon, a tubular form can be cast or otherwise formed from one or more materials of the described coating and disposed over the balloon prior to placement of the outer sheath. In one embodiment such tubular forms would be made by solvating the coating material(s) into a viscous state and through processes known to the art such as gel extrusion, casting, molding or solution casting/forming formed into the desired tubular shape. The solvent(s) used are subsequently removed to dry or partially dry the tube and makes it easy to dispose over the balloon. During use, the tube is rehydrated much like the coatings used with the invention and described herein.

In another embodiment, the structural layer is treated, coated, imbibed and/or filled with a wetting agent that can be cross-linked to allow instantaneous wetting (i.e., in less than about 10 seconds) of the outer sheath following contact with an aqueous medium. Such wetting agents include those described in U.S. Pat. No. 7,871,659, and U.S. Pat. No. 5,897,955, both of which are hereby incorporated by reference in their entireties for all purposes. In one embodiment, said wetting agent includes, but is not limited to poly(vinyl alcohol) polyethylene glycol, heparin, heparin coatings (such as those described in U.S. Pat. No. 6,461,665), polypropylene glycol, dextran, agarose, alginate, polyacrylamide, polyglycidol, poly(vinyl alcohol-co-ethylene), poly(ethyleneglycol-co-propyleneglycol), poly(vinyl acetate-co-vinyl alcohol), poly(tetrafluoroethylene-co-vinyl alcohol), poly(acrylonitrile-co-acrylamide), poly(acrylonitrile-co-acrylic acid-co-acrylamidine), polyacrylic acid, poly-lysine, polyethyleneimine, polyvinyl pyrrolidone, polyhydroxyethylmethacrylate, and polysulfone, and their copolymers, either alone or in combination. In another embodiment, said wetting agent includes glycols, fatty acid salts, and fatty alcohols, and combinations thereof.

The outer sheath and/or the structural layer can be made from any of the appropriate materials disclosed herein. These structures can be made by extrusion or by layering any of the material described above, e.g. ePTFE. A layer is considered one thickness of a material which may be wrapped, folded, laid or weaved over, around, beside or under another thickness. A longitudinal pass comprises a distinctive layer or series of layers of material which are wound to form a region or area distinct from surrounding or adjoining parts. For instance, a pass may comprise multiple layers of a material wrapped at a desired 90° angle relative to the longitudinal axis. This exemplary pass may then be flanked by layers of balloon material wrapped at dissimilar angles in relation to the longitudinal axis, thus defining the boundary of the pass. These layers may be oriented helically or circumferentially (or 90 degrees from the longitudinal axis). In addition, the sheath or structural layer can be helically wrapped at a low or high angle. A low angle wrap of a longitudinally oriented membrane can yield a wrapped construct more distensible than a high angle wrap of a membrane of the same longitudinal orientation, all else being equal (depends on the strength orientation of the membrane). The angle of the wrap can also vary the amount of stored length/foreshortening, radially or longitudinally. One method for making the structural layer and outer sheath is described below in the examples. In one embodiment, said structural layer can vary in thickness along their longitudinal axes. This will allow for different shapes at the second, inflated diameter. In another embodiment, the construction of the structural layer and/or outer sheath is discontinuous along the longitudinal axis of the components, e.g., one section of the outer sheath is thicker or comprises a different material, or is thinner than another section. In another embodiment, the ends of the structural layer and/or outer sheath are modified to decrease profile of the agent delivery device at the points on the underlying catheter where the structural layer and/or outer sheath are attached. For example, if the structural layer and/or outer sheath are constructed as tubes, a portion of the circumference of their ends may be skived away to open up the tube, i.e., making the ends of the tube only a portion of their original, full circumference. These end "tabs" are then attached to the catheter (using a method detailed below). Because these tabs comprise less material, the profile at the region of their attachment is decreased. In another embodiment, discrete perforations are created in the outer sheath, further modulating its capacity to deliver a coating and/or therapeutic agent to the surrounding tissue.

To make the agent delivery construct of the present invention, a hydrophilic layer is formed on an expandable member or a structural layer by applying a hydrophilic substance comprising a therapeutic agent. The hydrophilic layer is applied to the surface of the balloon or a structural layer. The hydrophilic substance may then be optionally bound in place, such as through cross-linking. For a porous surface, the hydrophilic layer may optionally be adsorbed within the porous void spaces of the surface. Coating a balloon or structural layer is described in detail in the examples below.

Suitable components for the hydrophilic coating include, but are not limited to, ionic surfactants including benzethonium chloride (e.g. HYAMINE®), benzalkonium chloride, cetylpyridinium chloride, cetalkonium chloride, laurtrimonium bromide, myristyltrimethylammonium bromide, cetrimide, cetrimonium bromide, stearalkonium chloride, n,n-diethylnicotinamide, cholesterol, calcium salicylate, methyl salicylate, sodium salicylate, sodium benzoate, benzoic acid, α-tocopherol, thiamine, niacinamide, dimethyl sulfoxide, decyl methyl sulfoxide, poloxamers (such as 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407), sorbitan monolaurate, sorbitan monostearate, sorbitan tristearate, octoxynols (such as Triton X-100 and Triton X-405), polysorbate 20, polysorbate 40, polysorbate 60, polysorbate 80, polyvinyl alcohol, polyvinylpyrrolidone, polyethylene glycol (PEG, molecular weight ranges from 400-50,000, with preferred from 700-15,000), PEG-amine, PEG-modified biopharmaceuticals and/or molecules, PEG amines (that include azido PEG amines and PEG diamines), JEFFAMINES® which are polyoxyalkyleneamines, quartenary ammonium compounds, 1,2-ditetradecanoyl-sn-glycero-3-phosphocholine, 1,2-dimyristoyl-sn-glycero-3-phospho-rac-(1-glycerol), 1,2-dimyristoyl-sn-glycero-3-phosphocholine, polypropylene glycol, heparin, or heparin derivatives, dextran, lactic acid, citric acid, ascorbyl palmitate, mannitol, palmitic acid, poly acrylic acid (Carbomer), gentisic acid, deoxycholic acid, glucuronic acid, amino acids, (such as histidine, lysine, arginine, glutamate, etc), polymeric chains of amino acids (such as polyarginine, polyglutamate), gluconolactone, agarose, stearic acid, stearyl alcohol, edetate disodium dehydrate edentate, hetastarch, phospholipids, cholesterol, liposomes, inclusion complexes such as cyclic oligosaccharides like cyclodextrin and its derivatives, including hydroxypropyl-β-cyclodextrin (HPβCD), Captisol® (a trademark of CyDex Pharmaceuticals, Inc.), dimethyl-β-cyclodextrin, α-cyclodextrin (αCD), alginate, polyacrylamide, polyglycidol, poly(vinyl alcohol-co-ethylene), poly(ethyleneglycol-co-propyleneglycol), poly(vinyl acetate-co-vinyl alcohol), poly(tetrafluoroethylene co-vinyl alcohol), poly(acrylonitrile-co-acrylamide), poly(acrylonitrile-co-acrylic acid-co-acrylamide), polyacrylic acid, poly-lysine, polyethyleneimine, polyvinyl pyrrolidone, polyhydroxyethylmethacrylate, cyclodextrins, γ-cyclodextrin, sulfobutylether-β-cyclodextrin, and polysulfone, polysaccharides, and their copolymers, shellolic acid, ipromide, urea, either alone or in combination. Other coatings are known in the art, see, e.g., U.S. Patent Publication 20100233266, which is hereby incorporated by reference in its entirety for all purposes, can also be used as part of this invention. In another embodiment, said hydrophilic coating is a heparin coating, such those described in U.S. Pat. Nos. 4,810,784 and 6,559,131.

In another embodiment, hygroscopic substances may be incorporated in the coating to accelerate fluid uptake. These materials include, but are not limited to saccharides, dimethyl sulfoxide, decyl methyl sulfoxide, polyvinyl alcohol, glycerol, many salts, including, but not limited to, sodium chloride, zinc chloride, and calcium chloride. Such hygroscopic substances will attract and hold water molecules from the surrounding environment through either absorption or adsorption and help in hydrating said dehydrated coating.

Such hygroscopic substances may be combined with any of the excipients described herein and/or commonly known in the art.

In another embodiment, the coating can comprise drug binding agents which act to bind drug particles to one another.

In another embodiment, the coating can comprise a tissue uptake enhancer to increase the dwell time of the therapeutic agent on tissues, tissue uptake of the therapeutic agent, or drug efficacy. Tissue uptake enhancers include integrins, lectins, osmotic agents, membrane disrupters, vasodilators, or polyethylene glycol conjugates. Such uptake enhancers may also include but are not limited to mannitol, decyl methyl sulfoxide, dimethyl sulfoxide, histidine, lysine, lysine acetate, arginine, polyarginine, polyglutamate, poly (glutamate-PEG), sorbitan monostearate, sorbitan tristearate, ascorbyl palmitate, palmitic acid, poly acrylic acid (Carbomer), deoxycholic acid, glucuronic acid. In another embodiment, a therapeutic agent can be complexed with or bonded to a tissue uptake enhancer.

In other embodiments, the coating can comprise a thixotropic agent, mucoadhesive or other agent to enhance the amount of time the coating remains in contact with target tissues, i.e., "dwell time". Such thixotropic agents or mucoadhesive agents may include but are not limited to hetastarch, alginate, poly acrylic acid (Carbomer), polyvinylpyrrolidone (PVP), inclusion complexes of PEG and a cyclodextrin, and biochemically reactive PEG In another embodiment, agents can be incorporated in the coating which serve to bind particles of a therapeutic agent to a target tissue.

In another embodiment, the coating can comprise a stabilizing agent to extend the "shelf life" of a device, such as antioxidants or other known preservatives.

Differential Scanning calorimetry (DSC) can be used to identify and characterize complexes and other physical states of the coating. Fourier Transform Infrared Spectroscopy (FTIR) or Nuclear Magnetic Resonance (NMR) may also be utilized to further characterize complex formation, micelle formation, hydrotrophs, and other formations, which alter the morphology of the therapeutic agent, and to characterize the coating.

A "therapeutic agent" as used herein, which is used interchangeable with the term "drug", is an agent that induces a bioactive response. Such agents include, but are not limited to, cilostazol, everolimus, dicumarol, zotarolimus, carvedilol, anti-thrombotic agents such as heparin, heparin derivatives, urokinase, and dextrophenylalanine proline arginine chloromethylketone; anti-inflammatory agents such as dexamethasone, prednisolone, corticosterone, budesonide, estrogen, sulfasalazine and mesalamine, sirolimus and everolimus (and related analogs), anti-neoplastic/antiproliferative/anti-miotic agents such as major taxane domain-binding drugs, such as paclitaxel and analogues thereof, epothilone, discodermolide, docetaxel, paclitaxel protein-bound particles such as ABRAXANE® (ABRAXANE is a registered trademark of ABRAXIS BIOSCIENCE, LLC), paclitaxel complexed with an appropriate cyclodextrin (or cyclodextrin like molecule), rapamycin and analogues thereof, rapamycin (or rapamycin analogs) complexed with an appropriate cyclodextrin (or cyclodextrin like molecule), 17β-estradiol, 17β-estradiol complexed with an appropriate cyclodextrin, dicumarol, dicumarol complexed with an appropriate cyclodextrin, β-lapachone and analogues thereof, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, AZX100 a cell peptide that mimics HSP20 (Capstone Therapeutics Corp., USA), heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; agents that interfere with endogenous vasoactive mechanisms; inhibitors of leukocyte recruitment, such as monoclonal antibodies; cytokines; hormones or a combination thereof. In one embodiment, said therapeutic agent is a hydrophilic agent. In another embodiment, said therapeutic agent is a hydrophobic agent. In another embodiment, said therapeutic agent is paclitaxel.

Most microporous materials will eventually wet-out with body fluids following implantation. However, this process may require significant time (hours to days). In the case of some fluoropolymers, such as ePTFE, its hydrophobic nature can greatly slow the process of replacing air with fluid, which may slow or completely restrict therapeutic agent release from a coated expandable member, e.g. balloon, underlying under the outer sheath. However, if the ePTFE is wet too quickly, which can occur when the micropores are too large, then premature drug release may occur before balloon catheter is positioned at the desired location.

Figure 2A:
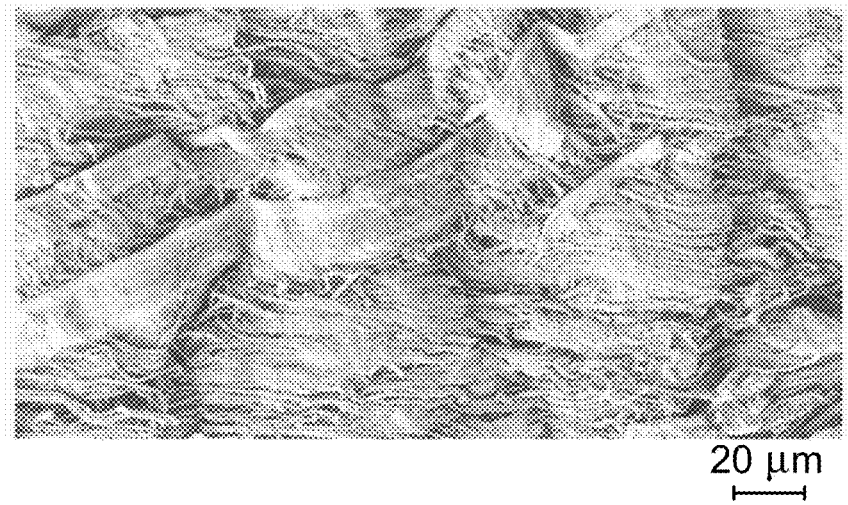
FIGS. 2A and 2B show micrographs of embodiments of a selectively permeable microstructure.
Figure 2B:
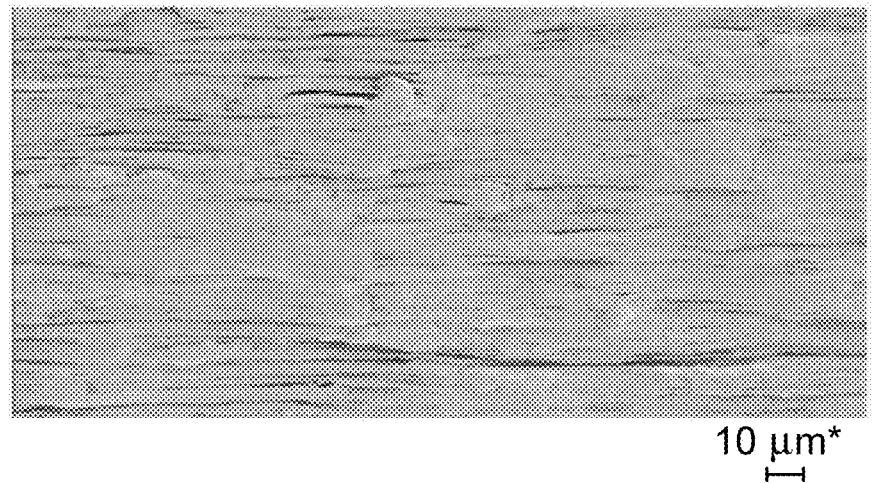

In one embodiment, the outer sheath comprises a tight porosity that permits the inflow of fluid and limits or restricts the outflow of a hydrated or partially hydrated coating. Stated another way, the outer sheath restricts particulation, e.g., release of particles greater than about 5 μm or 10 μm or about 25 μm, of a coating during tracking. This hydration mechanism results from the novel combination of an at least partially permeable, microporous material in the outer sheath with a dehydrated hydrophilic coating underneath or within the outer sheath. In one embodiment, once the hydrophilic coating begins to become, or is fully hydrated, the tight porosity of the outer sheath at its first state, as shown in FIGS. 2A and 2B, serves as a bulk fluid transfer barrier to the hydrated or partially hydrated coating and/or the therapeutic agent associated therewith. FIGS. 2A and 2B are scanning electron micrographs (SEMs) of permeable microstructures that comprise ePTFE. These microstructures comprise micropores which permit, at least partially, displacement of the air within the micropores. When this occurs, the outer sheath can be at least partially wetted, facilitating hydration or partial hydration of the coating.

Upon or after expansion (i.e., inflation of the medical balloon), the outer sheath retracts and exposes coating or coating and therapeutic agent to the surrounding environment. Such transfer occurs with minimized particulation, being that the coating can be hydrated prior to being exposed to the surrounding environment.

In the embodiment in which the expandable member is a balloon and the outer sheath comprises ePTFE, when the balloon is in its first state, the ePTFE comprising outer sheath has a tight microstructure that permits the outer sheath to at least partially wet out and the hydrophilic coating to at least partially hydrate but serves as a barrier to the bulk fluid flow of the hydrated or partially hydrated coating through the outer sheath. Once the balloon is positioned at the treatment site, the balloon can be inflated and the sheath can be retracted, thereby exposing the hydrated coating to the surrounding tissue. This embodiment enables consistent, controlled on-demand drug delivery to a target site (e.g. a body vessel).

In an embodiment, the selectively permeable outer sheath can be configured to retract in a number of ways. A few retractable outer sheath embodiments are described below.

Figure 3A:
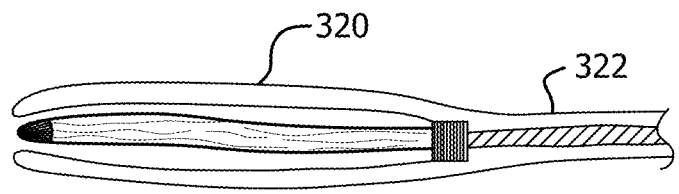
FIGS. 3A to 3C illustrate cross-sectional views of an embodiment comprising an outer sheath having a tubular form coupled to a retraction member shown in a covered (3A and 3B) and retracted state (3C).
Figure 3B:
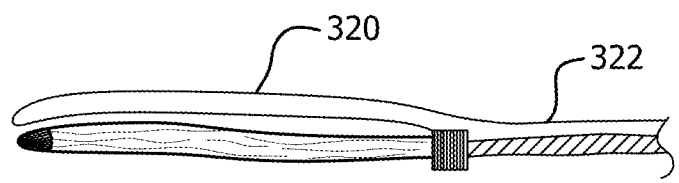
Figure 3C:
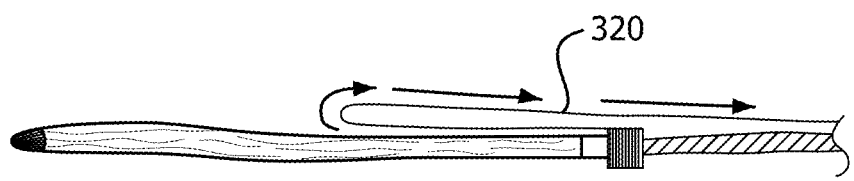

In an embodiment, with reference to FIG. 3A to 3C, the outer sheath 320 can comprise a tubular form that can be coupled to a retraction member 322. Axial displacement of the retraction member 322 causes axial displacement of the tubular form. Tubular form can comprise a single-walled member, double walled member, or other multiply construct. Double-walled construction can be configured to retract via eversion, as is depicted in FIG. 3A to 3C.

Figure 4A:
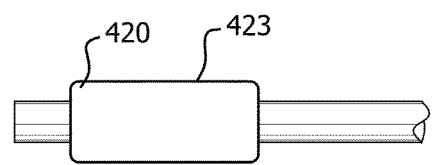
FIGS. 4A and 4F illustrate side views of an embodiment comprising an outer sheath having a neckable element helically wrapped around an expandable member shown in an unexpanded (4A, 4C, and 4E) and expanded state (4B, 4D, and 4F).
Figure 4B:
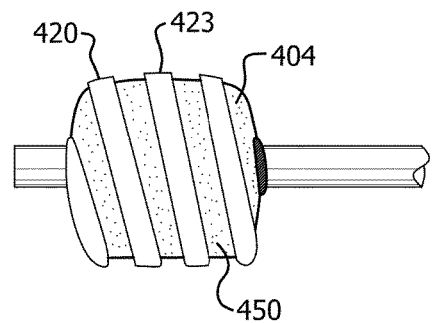
FIGS. 4G and 4J illustrate side views of an embodiment comprising an outer sheath having at least two neckable annular elements adjacent to each other shown in an unexpanded (4G and 4I) and expanded state (4H and 4J).
FIGS. 4K and 4L illustrate side views of an embodiment comprising an outer sheath having at least two neckable elements longitudinally oriented and adjacent to each other in an unexpanded (4K) and expanded state (4L).
Figure 4C:
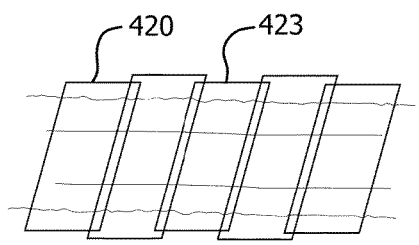
Figure 4D:
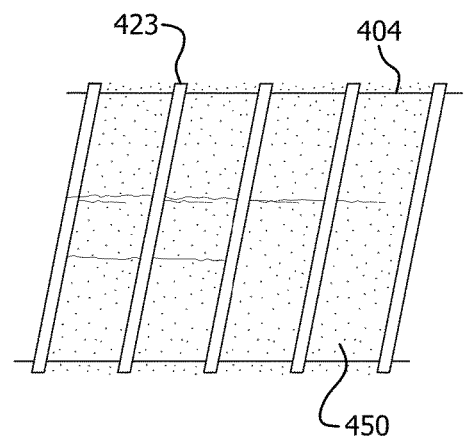
Figure 4K:
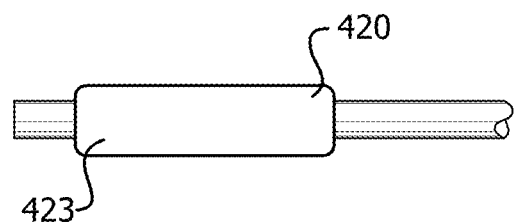
Figure 4L:
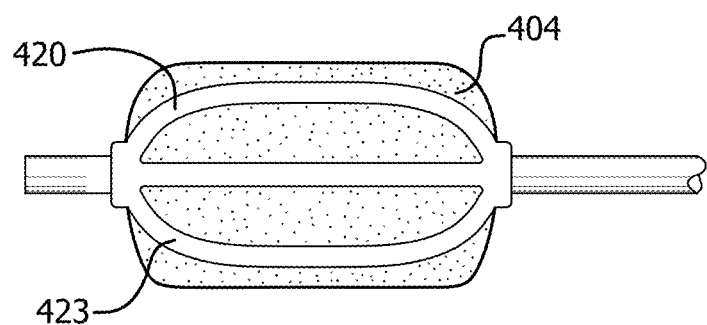

In an embodiment, with reference to FIGS. 4A and 4L, the outer sheath 420 can comprise neckable element 423. Said neckable element 423 is any elongated element configured to reduce in the width dimension as it lengthens. As the underlying expandable member 404 increases in effective surface area or circumference (whether expandable member elastically expands or un-pleats or unfolds), the retractable sheath 420 comprising neckable elements 423 does not correspondingly increase in surface area or circumference, thereby exposing at least a portion of the underlying surface, e.g., a coating 450. As previously described, in an embodiment, the outer sheath 420 can be coated with a wetting agent to facilitate wetting of the sheath and hydration of the coating.

Said neckable element 423 can comprise a strip of film. Said strip can be single-ply or multi-ply. Said film can comprise a plastic and/or an elastic material. Specific neckable materials can include ePTFE membranes, ePE, Polyamides, Polyurethanes, Silicones, Polyethylene, or any other sheet or film material possessing the neckable properties. Said film can be an anisotropic material oriented along the expandable member 404 wherein strain can be applied in the weaker direction. On the other hand, balanced materials can also be utilized. Neckable elements 423 can have an initial width of, for example, at least about 1 μm to about 10 mm or more. Neckable element 423 can undergo, for example, at least a 2-, 5, 10-, or 15-fold reduction in width during expansion. Upon expansion of the expandable member 404, the underlying surface, e.g., coating 450, is exposed due to the neckable elements 423 becoming strained and reducing in diameter. The neckable element 423 can be selectively permeable as described herein, thus providing for hydration of an underlying coating 450.

In an embodiment, said neckable element 423 can comprise a flattened tubular form. Said tubular form can be formed from a helically wrapped tape and then flattened and disposed about the expandable member, in a longitudinal, circumferential, or helical fashion to form the outer sheath 420. The wrap angle can contribute to the degree of necking. For example, a tubular form can be formed at a high helical wrap angle, and upon expansion, tension is applied to the tubular form, causing the helical angle to change to a lower angle and the diameter of the tubular form to reduce. In an embodiment, coating 450 can also be located within the lumen of the tubular form.

In an embodiment, with reference to FIGS. 4A and 4F, said neckable element 423 or a plurality of neckable elements 423 can be helically wrapped around an expandable member. For example, a helically wrapped, flattened tubular form can be helically wrapped around an expandable member 404. Neckable elements 423 can be constructed to have any suitable width to cover the expandable member 404 with the desired number of helical turns. The smaller the width and the higher the number of helical turns lessens the discontinuity of direct contact between a therapeutic agent and a surrounding tissue upon retraction.

Similarly, in an embodiment, with reference to FIGS. 4G and 4L, at least two neckable elements 423 can be longitudinally oriented and adjacent to each other along the expandable member 404 and attached at a proximal and distal ends of the expandable member 404. In another embodiment, with reference to FIGS. 4G and 4H, said retractable sheath 420 can comprise at least two adjacent annular neckable elements 423. Neckable elements 423 can be constructed to have any suitable width to cover the unexpanded expandable member 404 with the desired number of adjacent elements 423. The smaller the width and the higher the number of adjacent elements 423 allows for more continuous contact of a therapeutic agent to a surrounding tissue.

In an embodiment, the sheath 420 is comprised of a netting or weave of neckable elements 423 where the interstitial spaces open upon stretching. Said neckable elements 423 can be neckable filaments. Said filaments can be sub-micron in width if desired, e.g., 0.1 µm.

Figure 5A:
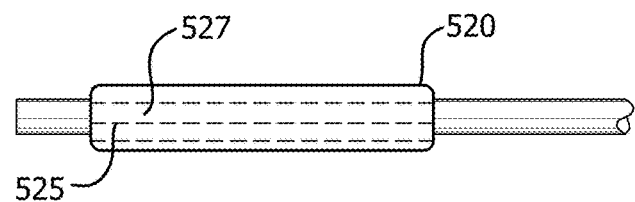
FIGS. 5A to 5B, illustrate an embodiment comprising an outer sheath having splittable cover in an unexpanded (5A) and expanded state (5B).
Figure 5B:
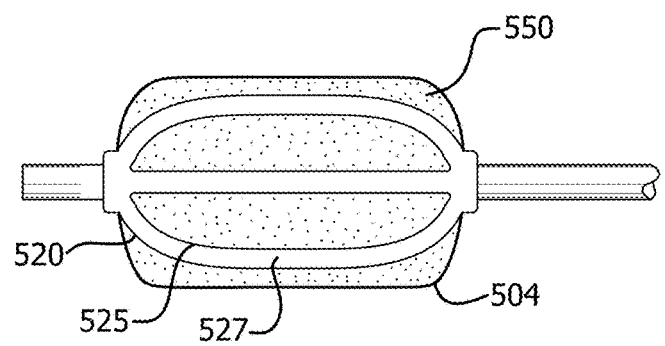

In an embodiment, with reference to FIG. 5A to 5B, the outer sheath 520 can comprise splittable cover. Said splittable cover can comprise a film member 527 or a plurality of film members 527 that have a seam 525 about which the cover will separate and/or split open when the expandable member 504 expands. In one embodiment, seams 525 can be formed at adjacent film members 527. An adhesive can be used to maintain a seam 525 that will not separate or rupture until expansion. In other embodiments, seams 525 can be formed at structurally weakened areas of the film member 527. Structurally weakened areas can comprise a plurality of perforations or thinned regions that rupture upon expansion. Seams 525 can be oriented longitudinally or at a low helical angle. Film member 527 may or may not be neckable. In an embodiment comprising a balloon which is pleated and folded into a collapsed position, the overlying retractable sheath 520 can comprise a plurality of seams 525 that coincide with a plurality of pleats on the underlying balloon in order to facilitate splitting. In an embodiment, hydration of an underlying coating 550 may occur at the site of seams 525 if desired. In another embodiment, the film members 527 can be selectively permeable as described herein.

In an embodiment, a splittable cover 525 can comprise at least two cover elements 527, each having an edge 525, wherein the edges 525 are adjacent. Upon expansion of an expandable member 504, the edges 525 separate and expose an underlying surface. The cover elements 527 can be neckable, which further increases the separation distance between two cover elements 527 upon expansion. In an embodiment, hydration of an underlying coating 550 may occur at the site of adjacent edges 525 if desired. In another embodiment, the cover elements 527 can be selectively permeable as described herein.

Figure 6A:
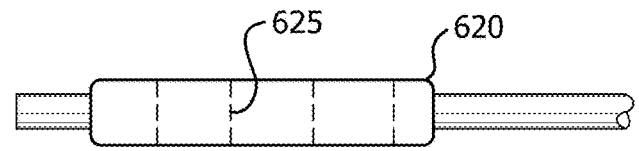
FIGS. 6A and 6B illustrate an embodiment comprising an outer sheath having a neckable cover with structurally weakened seams in an unexpanded (6A) and expanded state (6B).
Figure 6B:
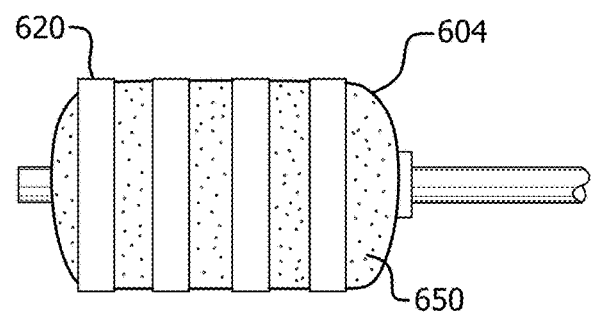

In an embodiment, with reference to FIGS. 6A and 6B, said outer sheath 620 if formed by a neckable sleeve having structurally weakened seams 625 in at least one of a circumferential, longitudinal, or helical pattern. Said structurally weakened seams 625 will rupture as the expandable member 604 expands, necking the outer sheath 620 fragmented sections and exposing the underlying coating 650. In an embodiment, hydration of an underlying coating 650 may occur at the site of seams 625 if desired. In another embodiment, the outer sheath 620 can be selectively permeable as described herein.

Figure 7A:
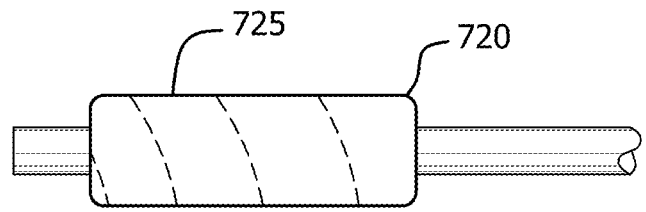
FIGS. 7A to 7B, illustrate an embodiment comprising an outer sheath having a splittable casing in an unexpanded (7A) and expanded state (7B).
Figure 7B:
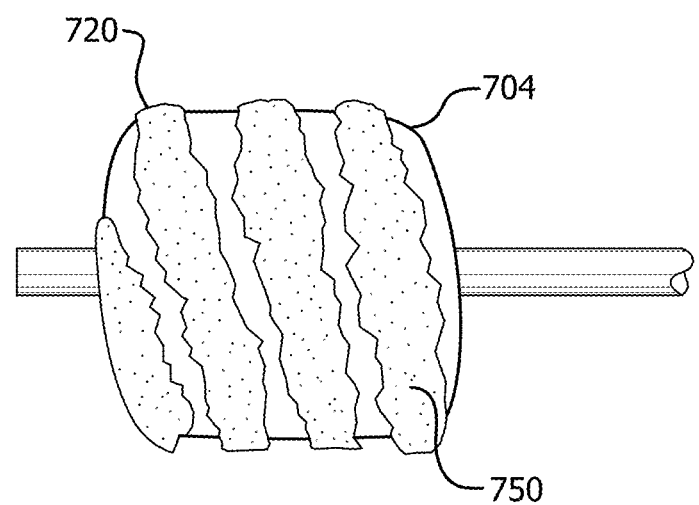
Figure 7C:
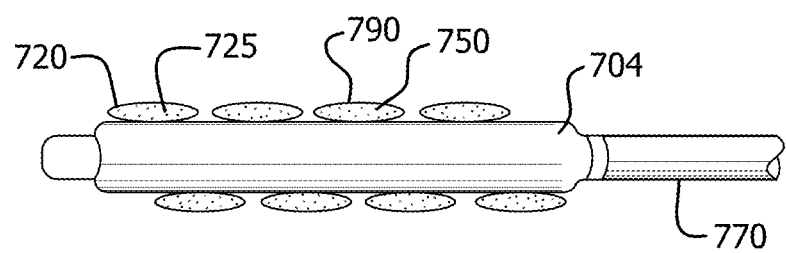
FIGS. 7C to 7D, illustrate a lengthwise, cross-sectional view of an embodiment comprising an outer sheath having a splittable casing in an unexpanded (7C) and expanded state (7D).

In an embodiment, with reference to FIG. 7A to 7B, the outer sheath 720 can comprise a splittable casing. Said casing comprises a two layered construct, having at least an inner face and an outer face and at least partially defining an interior space or lumen. The casing comprises a seam 725 configured to split or rupture along a dimension, e.g., its length, and is positioned on the expandable member 704 so that said seam 725 faces in an outward direction. A coating 750 comprising a therapeutic agent can be located within the lumen 790 of the casing as shown in FIG. 7C. Upon expansion, said casing can spit open and/or rupture along seam 725, exposing the coating 750 to the surrounding environment. As previously described, the seam 725 can be a structurally weakened section. The casing can be oriented longitudinally, helically, or circumferentially relative to the longitudinal axis of the expandable member 704. In an embodiment, hydration of an underlying coating 750 may occur at the site of seams 725 if desired. In another embodiment, the casing (composing the outer sheath 720) can be selectively permeable as described herein.

Figure 7D:
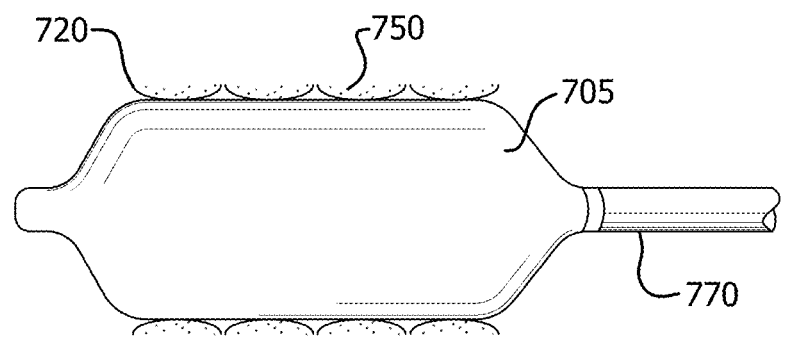
Figure 8A:
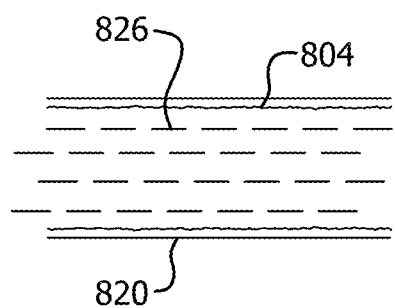
FIGS. 8A to 8D illustrate an embodiment comprising an outer sheath having at least one dilatable feature in an unexpanded (8A and 8C) and expanded state (8B and 8D).
Figure 8B:
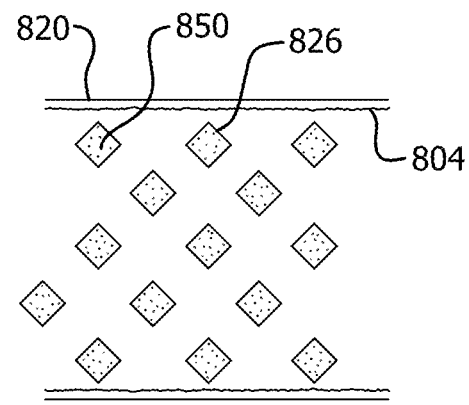
Figure 8C:
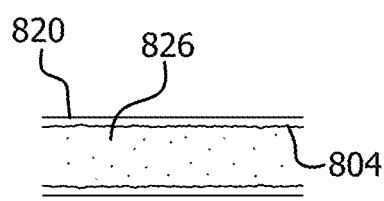
Figure 8D:
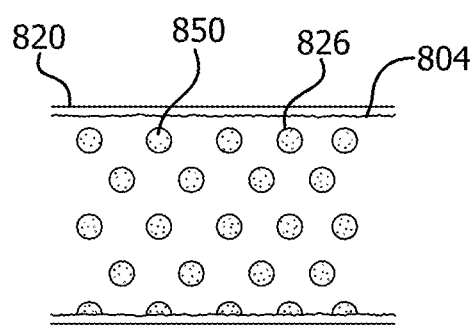

For example, in an embodiment, the casing can be a form having a lumen 790 and a rupturable seam 725 along its length, as shown in FIGS. 7C and 7D, taken at lengthwise cross section FIGS. 7A and 7B, respectively. Also shown in FIGS. 7C and 7D are the expandable member 704 and a catheter 770. Said tubular form can be flattened and disposed about the expandable member 704 to form an outer sheath 720 in a manner where the seam 725 faces outward. Said tubular form can be helically wrapped around the expandable member to form the outer sheath. In other embodiments, said tubular form can be formed into a ring shape and can be circumferentially disposed around balloon. In another embodiment, said tubular form can be longitudinally oriented about the balloon, e.g., attached at a proximal and distal end of a catheter and mounted across the length of the expandable member.

In an embodiment, with reference to FIG. 8A to 8D, the outer sheath 820 can comprise at least one dilatable feature 826, such as a dilatable pore or slit. Upon expansion of the expandable member 804, dilatable feature 826 will form an opening 827 through which the underlying layer or surface, e.g., coating 850, is exposed. In an embodiment, the outer sheath 820 material cannot stretch to a high enough extent without the propagation of tears or 'openings' that occur at predefined dilatable features 826. In an embodiment, a microporous tubing of a microstructure that allows for hydration at a first diameter can be used as an outer sheath 820. This tube may only be capable of distention to an intermediate diameter. This same tubing with dilatable features 826, such as laser cut slits, may allow the cover to distend to the intended second diameter. Upon expansion, the underlying surface will be exposed in the newly uncovered surface area In an embodiment, hydration of an underlying coating 850 may occur at the site of dilatable feature 826 if desired. In another embodiment, the outer sheath 820 can be selectively permeable as described herein. In another embodiment, the outer sheath 820 can be coated with a wetting agent to facilitate wetting of the sheath and hydration of the coating.

In another embodiment, a hydrophilic coating or a hydrophilic coating in combination with a therapeutic agent can be applied to only a portion of an expandable member, e.g., the surface of the balloon, in a discontinuous fashion. Upon retraction, the coating and/or therapeutic agent are delivered to a discrete or more localized site. In contrast, when the coating and/or therapeutic agent is applied in an even distribution to the entire surface of the expandable member, a more uniform delivery of the coating and/or therapeutic agent from the entire circumference of the expandable member can be achieved.

Thus, one embodiment of the invention comprises the drug delivery system comprising an expandable member, such as a balloon, which may comprise a structural layer and/or a substrate, at least one dehydrated or partially dehydrated hydrophilic coating containing at least one therapeutic agent, said coating located on the expandable member or structural layer and/or substrate, and an outer sheath with a permeable microstructure which is expandable by the expandable member. In its unexpanded state, the sheath is permeable to bodily fluids but limits the passage of the coating and therapeutic agent through the sheath. In one embodiment, the hydrophilic coating becomes at least partially hydrated prior to the sheath being expanded, but the coating and the therapeutic agent do not pass (or substantially pass) through the outer unexpanded sheath. Upon expansion, the sheath is retracted, e.g., in a manner as described herein, and the therapeutic agent in the coating is delivered to the treatment site. In another embodiment of the invention, the lowering of the fluid entry pressure of the sheath is effected via wetting of the outer sheath by a wetting agent applied to said outer sheath. In another embodiment, the wetting agent on said outer sheath comprises poly(vinyl alcohol) (PVA) or a heparin coating.

In another embodiment of the invention, the fluid entry pressure of the sheath can be tailored by selection of a suitable porous, hydrophilic material which does not require a wetting agent to function in accordance with the invention. For example, hydrophilic membranes comprising an expanded functional TFE copolymer may be used to construct the sheath. Such membranes are disclosed in U.S. Patent Publication 2012/0035283, hereby incorporated by reference in its entirety In another embodiment of the invention, a hydrophobic drug is sequestered by or complexed with one or more solubilizing agents such that when delivered to the intended tissue site the drug dissociates from the solubilizing agent and binds to tissue. Such solubilizing agents are known in the art (see, e.g., U.S. Patent Publication 20080118544).

In another embodiment, said coating comprises a hydrophilic component. In another embodiment, said coating comprises at least one compound selected from the group consisting of benzethonium chloride, poloxamer-188, polyethylene glycol, sodium salicylate, and hydroxypropyl-β-cyclodextrin. In another embodiment, said therapeutic agent is a hydrophilic agent. In another embodiment, said therapeutic agent is a hydrophobic agent. In another embodiment, said therapeutic agent is paclitaxel or a taxane domain-binding drug. In another embodiment, said expandable member further comprises a structural layer. In another embodiment, said structural layer comprises said coating and therapeutic agent.

As used herein, the terms "rapid" and "rapidly" refer to a clinically relevant timeframe, e.g., less than about 5.0 minutes. In another embodiment, the terms "rapid" and "rapidly" are defined herein to mean about 90, about 60, about 50, about 45, about 30, about 20, or about 10 seconds.

In some embodiments, the outer sheath will not be fully wet out. As further described below, very small, microscopic areas of the outer sheath can be wetted out. As used herein the term, "microscopic-wetting" refers to small areas of the outer sheath which wet, (i.e., air is replaced by liquid fluids) but these wet areas are so small that such wetting, that may be indicated by translucence of the wetted material (depending on the material), will not be visible to naked eye. In one embodiment, the outer sheath is composed of ePTFE which may undergo microscopic wetting, and thus, the outer sheath will not become translucent. Microscopic-wetting can occur when the outer sheath is in its first diameter and may contribute to pre-hydration of the coating. As will be further described below, this occurs in areas of the outer sheath where the micropores are large enough to allow air displacement by fluids.

As used therein the term "macroscopic wetting" is when the outer sheath is wet and wetting can be detected by the naked eye, for example, by at least a portion of an ePTFE comprising outer sheath becoming translucent. Macroscopic Wetting can be In some instances, the outer sheath, by design or due to variations in manufacturing, may have pores that allow microscopic wetting by fluids. This allows the fluids to enter through the outer sheath and to the coating, thus pre-hydrating the coating. Therefore, as the agent delivery construct of the invention is being tracked to the desired location, body fluids may be pre-hydrating the dehydrated or partially-dehydrated hydrophilic coating. Thus, one embodiment of the invention provides for pre-hydration of the hydrophilic coating provided by body fluids as the agent delivery construct of the invention is being tracked to the target site. As used herein the term "pre-hydration" means that the hydrophilic coating is hydrated or partially hydrated while the expandable member and the outer sheath are in their first, unexpanded state. In this embodiment, in their first, unexpanded state, the coating and/or therapeutic agent will not be released to an area external to the outer sheath in significant quantities. It will be appreciated by one of skill in the art that pre-hydration might be accomplished in whole or in part during preparation of the device prior to introduction into a patient.

Depending on the nature of the microstructure or coating and therapeutic agent formulation, solely relying on a microporous microstructure may be insufficient to achieve desired pre-hydration due to variability in manufacturing of a microporous structure, such as ePTFE. Thus, in one embodiment, a portion of the outer sheath (exterior area) is treated with a wetting agent. Suitable wetting agents include a hydrophilic coating or others well known in the art. That portion of the sheath "imbibed," "filled" or treated by the wetting agent will instantaneously (i.e., in less than about 10 seconds) wet-out when contacted by bodily fluids ("point wetting"). In turn, this allows said bodily fluids to pass through the sheath and into the hydrophilic coating, thus causing said coating to hydrate or partially hydrate. In another embodiment, the hydrophilic coating will fully hydrate, even if such "point wetting" is employed. This is because even small amounts of bodily fluids in contact with the coating are rapidly transported throughout the coating, hydrating the coating to some degree. Because the rest of the sheath remains unexpanded and/or unwetted, the now hydrated or partially hydrated coating remains substantially on the inside of the outer sheath until it is expanded by mechanisms described above. In another embodiment, said fluid is a vapor that can pass through the outer sheath and condense on the dehydrated coating. In this embodiment, the outer sheath may not become wet but allows for coating hydration. In another embodiment, conditioning the outer sheath with a wetting agent can be varied and/or patterned along the length and surface area of the outer sheath so that wetting of said outer sheath is uneven. This may help in adjusting the rate of wetting, the rate of delivery and/or amount of said therapeutic agent/coating delivered. In one embodiment, the outer sheath is partially conditioned with a wetting agent in a pattern along the outer sheath's surface to allow for "near instantaneous" wetting (i.e., in less than about 20 seconds).

In other embodiments, the entire outer sheath is treated, imbibed and/or filled with a wetting agent that can be cross-linked to allow instantaneous wetting (i.e., in less than about 10 seconds) of the outer sheath following contact with an aqueous medium, as described in U.S. Pat. No. 7,871,659, and U.S. Pat. No. 5,897,955, both of which are hereby incorporated by reference in their entireties for all purposes. In one embodiment, said wetting agent includes, but not limited to poly(vinyl alcohol) polyethylene glycol, heparin, heparin coatings (such as those described in U.S. Pat. No. 6,461,665), polypropylene glycol, dextran, agarose, alginate, polyacrylamide, polyglycidol, poly(vinyl alcohol-co-ethylene), poly(ethyleneglycol-co-propyleneglycol), poly(vinyl acetate-co-vinyl alcohol), poly(tetrafluoroethylene-co-vinyl alcohol), poly(acrylonitrile-co-acrylamide), poly(acrylonitrile-co-acrylic acid-co-acrylamidine), polyacrylic acid, poly-lysine, polyethyleneimine, polyvinyl pyrrolidone, polyhydroxyethylmethacrylate, and polysulfone, and their copolymers, either alone or in combination. However, the hydrated or partially hydrated coating and/or therapeutic agent will not be substantially transferred (or only a small amount may transfer) through the outer sheath in its first, unexpanded state because the outer sheath has closed microstructure and/or because there is no back pressure forcing the hydrated or partially hydrated coating to be transferred (e.g. pushed) outward.

In another embodiment of the invention, the fluid entry pressure of the sheath can be tailored by selection of a suitable porous, hydrophilic material which does not require a wetting agent to function in accordance with the invention. For example, hydrophilic membranes comprising an expanded functional TFE copolymer may be used to construct the sheath. Such membranes are disclosed in U.S. Patent Publication 2012/0035283, hereby incorporated by reference in its entirety In one embodiment, the portions of said outer, retractable sheath can permit said coating to pass through the microstructure during expansion. Without being bound to a particular theory, the transfer through the microstructure can be facilitated by a number of factors, e.g., the pressure form the underlying expandable member, the hydrophilic coating acting as a wetting agent, the downward pressure from the strained outer sheath, the shear forces at the interfaces of the outer sheath and coating as expansion occurs, and the opening of the tight microstructure. In this manner, the selectivity of the selectively permeable membrane can be varied by these factors. In one embodiment, once the hydrophilic coating begins to become, or is fully hydrated, the tight porosity of the outer sheath at its first state, as shown in FIGS. 2A and 2B, will serve as a bulk fluid transfer barrier to the hydrated or partially hydrated coating and/or therapeutic agent associated therewith. However, upon expansion (i.e., inflation of the medical balloon), the combination of the opening of the micropores, as shown in FIGS. 2C and 2D, with pressure-driven expansion, the hydrated or partially hydrated hydrophilic coating rapidly displacing air within at least a portion of the outer sheath (i.e., the coating wets-out the outer sheath) transfer of the coating or coating and therapeutic agent occurs through the portions of the outer sheath still covering a portion of the expandable member after expansion. In this embodiment, the hydrophilic coating is selected from a group that while being hydrophilic is also compatible with the sheath material to affect sheath wetting and subsequently provide for efficient coating transfer into and through the microstructure of the sheath. Such compatibility of coating to sheath material(s) can be tailored to meet the desired wetting characteristics (see, e.g., U.S. Pat. No. 5,874,165 which is hereby incorporated by reference in its entirety for all purposes).

It will be understood that the agent elution construct of the invention is not binary in its operation. Instead, while fluid transfer may be initiated at a discrete point in time, transfer rates will vary in accordance with the degree (and period of time) at which the microstructure of the outer sheath changes, e.g., opens and/or closes, is wet, or remains partially wetted, etc. Such changes may be controlled, for example, by varying the pressure of a semi-compliant expandable member. Such transfer rates can also be variably distributed across the surface of the outer sheath. For example, by selecting an outer sheath material which offers different pore sizes or pore densities in one region as compared to another, transfer rates between each region will be different. In another example, the outer sheath can comprise a composite or combination of materials, each with their own pore characteristics. An outer sheath with essentially uniform pore size and density can also be modified to provide variably distributed transfer, for example, by forming microbores in one surface region of the sheath while leaving the remaining regions unmodified. Microbores, as used herein, are formed holes that go straight through the sheath and can be formed by any known techniques, e.g., laser perforation.

In another embodiment, said outer sheath has small perforations, holes, slits, larger pores, or any other imperfection that allows body fluids to pre-hydrate the hydrophilic coating, without substantially allowing any therapeutic agent or coating particles to be released into the bloodstream while the balloon is in the first state. For example, an outer sheath can comprise a plurality of reinforced microbores. Reinforced microbores can be formed by laser perforating an outer sheath comprising ePTFE with a discontinuous layer of fluorinated ethylene propylene (FEP) on its surface. ePTFE coated with FEP is described in U.S. Pat. No. 5,735,892, which is hereby incorporated by reference in its entirety. The heat from the layer will melt the FEP along the perimeter of the microbore. The FEP melt can serve as a reinforcement, such that the pore may only minimally or negligibly increase in size as the expandable member expands. In an embodiment, microbores can be channels or passageways through which a hydrated or partially hydrated coating can be delivered to the surrounding tissue upon expansion. In such an embodiment, the outer sheath need not be retracted. Microbores, as used herein, are formed holes that go straight through the sheath and can be formed by any known techniques, e.g., laser perforation. In comparison, micropores are typically meandering and are part of the material's microstructure.

In an embodiment, controlled release of the inflation media from the underlying balloon, via perfusion, can also serve to pre-hydrate the coating. In another embodiment, the pre-hydration occurs due to purposeful leaking of a seal between the expandable member and the outer sheath.

In another embodiment, the microporous nature and/or "wettability" of the outer sheath may be distributed over only a portion or portions of the outer sheath. For example, certain locations on the surface of the microporous sheath material may be filled with another material (e.g., silicone and or polyurethane) and made non-microporous and/or non-wettable, but leaving the non-filled areas microporous. Similarly, changes in sheath surface structure (e.g., from "patterning" of the surface) may also be selectively located to create regions of the sheath which are not wettable. Such modifications to the sheath may be useful in instances controlling the rate that said outer sheath becomes wet. Thus, said outer sheath can be modified to have differential permeability throughout the entire outer sheath or can be patterned in such a way to allow for differential permeability at different locations throughout the outer sheath.

In another embodiment, the outer sheath is wet-out by a prescribed preparatory procedure prior to being inserted into the patient. In this embodiment, said agent delivery construct is prewetted in a sterile liquid (e.g. saline) supplied with said construct or in the patient's own blood.

In another embodiment of the invention, said coating comprises at least one hydrophilic component that raises the solubility point of a hydrophobic therapeutic agent. As used herein, the term "raises the solubility point of a hydrophobic therapeutic agent" means that there is an increase of concentration of a hydrophobic therapeutic agent at least 10% above the maximum solubility for said therapeutic agent in neat DI-water at room temperature and standard atmospheric conditions. This is usually due to the presence of an additional agent that allows for enhanced solubility (i.e., a hydrophilic component in said coating). This still allows for a portion of the therapeutic agent to not be dissolved into the water. For example, paclitaxel at room temperature in neat DI-water has a solubility limit of about 0.4 µM in water. The addition of hydroxypropyl-β-cyclodextrin at a concentration of 60% (w/v in water) raises the solubilized concentration of paclitaxel in solution to approximately 4 mM, well above a 10% increase in solubility (Sharma et al., Journal of Pharmaceutical Sciences 84, 1223 (1995)).

As used herein, weight percent (wt %) is the dry weight of a coating and/or therapeutic agent after solvent removal. In one embodiment, formulations comprising benzethonium chloride and a hydrophobic agent, such as paclitaxel, the preferred range for said hydrophobic agent are from about 1 wt % to about 70 wt %. In another embodiment, said hydrophobic agent, such as paclitaxel, ranges from about 40 wt % to about 70 wt %. In another embodiment, said hydrophobic agent, such as paclitaxel, ranges from about 20 wt % to about 40 wt %. In another embodiment, said hydrophobic agent, such as paclitaxel, ranges from about 1 wt % to about 20 wt %. In another embodiment, said formulations of benzethonium chloride and a hydrophobic agent, such as paclitaxel, is less than 20 wt % of said hydrophobic agent, such as paclitaxel. In another embodiment, said hydrophobic therapeutic agent is selected from the group consisting of taxane domain-binding drugs, such as paclitaxel, and rapamycin.

In another embodiment, formulations of poloxamer and of a hydrophobic agent, such as paclitaxel, range from about 1 wt % to about 70 wt %, from about 1 wt % to about 50 wt %, from about 1 wt % to about 40 wt %, from about 10 wt % to about 20 wt % of said hydrophobic agent, such as paclitaxel.

In another embodiment, formulations of poloxamer, PEG and of a hydrophobic agent, such as paclitaxel, range from: about 1 wt % to about 70 wt %, about 1 wt % to about 50 wt %, or about 8 wt % to about 40 wt % of a hydrophobic agent, such as paclitaxel; about 1 wt % to about 55 wt %, about 1 wt % to about 40 wt %, or about 5 wt % to about 30 wt % of PEG; and about 1 wt % to about 70 wt %, about 20 wt % to about 70 wt %, about 20 wt % to about 60 wt % of poloxamer, e.g. poloxamer-188. In another embodiment, said hydrophobic therapeutic agent is selected from the group consisting of taxane domain-binding drugs, such as paclitaxel, and rapamycin.

In one embodiment, the agent delivery construct of the invention comprises a coating comprising benzethonium chloride, and a hydrophobic therapeutic agent, wherein said hydrophobic therapeutic is less than 40 wt % of the dry coating. In another embodiment, said hydrophobic therapeutic agent is about 10 wt % to about 20 wt % of the dry coating and benzethonium chloride is about 80 wt % to about 90 wt % of the dry coating. In another embodiment, said hydrophobic therapeutic agent is selected from the group consisting of taxane domain-binding drugs, such as paclitaxel, and rapamycin.

In another embodiment, the agent delivery construct of the invention comprises a coating comprising poloxamer-188, and a hydrophobic therapeutic agent, wherein said hydrophobic therapeutic agent is less than 60 wt % of the dry coating. In another embodiment, said hydrophobic therapeutic agent is about 10 wt % to about 30 wt % of the dry coating and said poloxamer-188 is about 60 wt % to about 75 wt % of the dry coating. In another embodiment, said hydrophobic therapeutic agent is selected from the group consisting of taxane domain-binding drugs, such as paclitaxel, and rapamycin.

In another embodiment, the agent delivery construct of the invention comprises a coating comprising poloxamer-188 and PEG, and a hydrophobic therapeutic agent, wherein said hydrophobic therapeutic agent is less than 50 wt % of the dry coating. In another embodiment, said hydrophobic therapeutic agent is less than 50 wt % of the dry coating and PEG is less than 30 wt % of the dry coating. In another embodiment, said hydrophobic therapeutic agent is about 10 wt % to about 30 wt % of the dry coating and PEG is about 10 wt % to about 20 wt % of the dry coating. In another embodiment, said hydrophobic therapeutic agent is about 10 wt % to about 20 wt %, PEG is about 10 wt % to about 20 wt %, and poloxamer-188 is about 50 wt % to about 65 wt % of the dry coating. In another embodiment, said hydrophobic therapeutic agent is selected from the group consisting of taxane domain-binding drugs, such as paclitaxel, and rapamycin.

In another embodiment, the agent delivery construct of the invention comprises a coating comprising benzethonium chloride and PEG, and a hydrophobic therapeutic agent, wherein said PEG is less than 30 wt % of the dry coating and said hydrophobic therapeutic agent is less than 50 wt % of the dry coating. In another embodiment, said PEG is about 10 wt % to about 20 wt % of the dry coating and said hydrophobic therapeutic agent is about 10 wt % to about 25 wt % of the dry coating. In another embodiment, said PEG is about 10 wt % to about 20 wt % of the dry coating, said hydrophobic therapeutic agent is about 10 wt % to about 25 wt % of the dry coating, and benzethonium chloride is about 50 wt % to about 65 wt % of the dry coating. In another embodiment, said hydrophobic therapeutic agent is selected from the group consisting of taxane domain-binding drugs, such as paclitaxel, and rapamycin.

In another embodiment, the agent delivery construct of the invention comprises a coating comprising benzethonium chloride and poloxamer-188, and a hydrophobic therapeutic agent, wherein poloxamer-188 is less than 30 wt % and said hydrophobic therapeutic agent is less than 50 wt % of the dry coating. In another embodiment, poloxamer-188 is about 10 wt % to about 20 wt % of the dry coating and said hydrophobic therapeutic agent is about 10 wt % to about 35 wt % of the dry coating. In another embodiment, said poloxamer-188 is about 10 wt % to about 20 wt %, said hydrophobic therapeutic agent is about 10 wt % to about 25 wt %, and benzethonium chloride is about 50 wt % to about 65 wt % of the dry coating. In another embodiment, said hydrophobic therapeutic agent is selected from the group consisting of taxane domain-binding drugs, such as paclitaxel, and rapamycin.

In another embodiment, the agent delivery construct of the invention comprises a coating comprising hydroxypropyl-β-cyclodextrin, and a hydrophobic therapeutic agent, wherein said hydroxypropyl-β-cyclodextrin is equal to or less than 98 wt % of the dry coating. In another embodiment, said hydroxypropyl-β-cyclodextrin is less than 80 wt % of the dry coating. In another embodiment, said hydrophobic therapeutic agent is selected from the group consisting of taxane domain-binding drugs, such as paclitaxel, and rapamycin.

In another embodiment, the agent delivery construct of the invention comprises a coating comprising sodium salicylate, and a hydrophobic therapeutic agent, wherein said sodium salicylate is about 75 wt % to about 95 wt % of the dry coating. In another embodiment, said sodium salicylate is less than 80 wt % of the dry coating. In another embodiment, said hydrophobic therapeutic agent is selected from the group consisting of taxane domain-binding drugs, such as paclitaxel, and rapamycin.

The therapeutic agents useful in conjunction with the system of the invention may be delivered to the tissue in various structural forms, including but not limited to micelles, liposomes, micro-aggregates, nanospheres, microspheres, nanoparticles, microparticles, crystallites, inclusion complexes, emulsions, gels, foams, creams, suspensions, liquids, and solutions or any combination thereof. In one embodiment, the agent is delivered to the tissue in a solubilized form. In another embodiment, the agent is delivered to the tissue in a gel. In another embodiment, the agent is delivered to the tissue in a solubilized form that precipitates from solution into a solid form. In another embodiment, the agent is delivered to the tissue as a combination of solubilized and solid forms.

The "expandable member" according to the present invention can be a balloon, expandable catheter, stent, stent-graft, a self-expanding construct, a balloon expandable construct, a combination self-expanding and balloon expandable constructs, a blood vessel graft or a mechanical, radially expanding device which may be expanded, for example via application of a torsional or longitudinal force. Expandable members can also include those which expand due to pneumatic or hydraulic pressure, those which expand due to magnetic forces, those which expand due to the application of energy (for example electrical or ultrasonic (piezoelectric) energy), and those which expand due to osmosis. Expandable members can be placed temporarily in any lumen (e.g. a vessel) by expanding said device and then removed by collapsing said device by a torsional or longitudinal force. In one embodiment, a structural layer and outer sheath is placed on the device such that when it is expanded, the outer sheath retracts and a therapeutic agent will be delivered. In another embodiment, said expandable member allows for blood perfusion to downstream vasculature while implanted in said vessel. This feature may allow for longer implantation durations. In one embodiment, the expandable members may be detached in vivo, and optionally retrieved, from placement devices (e.g., catheters). Examples can be found in U.S. Pat. Nos. 3,996,938, 4,650,466, 5,222,971, and 6,074,339.

In one embodiment, the expandable member is a medical balloon. Balloons useful in the invention may be blow-molded, may be compliant or semi-compliant or non-compliant and may be of various shapes, for example so called "conformable" or "conforming" or "steerable" balloons. The physical characteristics of said expandable members may also be modified; for example, they may have modulus values which differ from one another. In other embodiments, the expandable members may comprise balloons which are constructed of wrapped films, are fiber-wound, are of variable length, are segmented, and/or have controlled, variable inflation profiles. Such inflation profiles can be, for example, middle-out, where the middle of the balloon increases in diameter first, followed by inflation toward and ultimately including the ends; distal to proximal where the distal end inflates first and inflation progresses proximally; proximal to distal where the proximal end of the balloon inflates first and inflation progresses distally; or ends to middle where both ends of the balloon inflate first and inflation progresses toward the middle of the balloon. Such a construct has the advantage of occluding or limiting flow through the vessel prior to a substantial portion of the therapeutic agent passing through the sheath. (In other words, a "no-flow" or "limited-flow" environment is created once the center portion of the balloon engages with the surrounding tissue.) For example a balloon that inflates first in its longitudinal center region, followed by the ends proximal and distal the center region will cause the coating or coating and therapeutic agent to contact the surrounding tissue first in the center region of the balloon. In other embodiments, a balloon can inflate preferentially in either the distal or proximal region, with the opposite region subsequently inflating. Other advantages of variable inflation profiles can be realized with use in tapered lumens, for the controlled delivery of endoprotheses, for ballooning of focal lesions with improved accuracy, or for the control of blood flow during the delivery of a therapeutic agent.

Balloons with controlled or variable inflation profiles can be constructed as follows. In one embodiment, a cover may be created by wrapping a film membrane around the balloon. The number of wrapped layers varies along the length of the balloon with fewer layers being positioned over the balloon where expansion is desired to occur first. For example, a middle-out inflation is achieved by wrapping a larger number of layers on the distal and proximal ends of the balloon, leaving fewer layers in the middle of the balloon. The stress exerted by the balloon on the cover layers during balloon inflation meets a lower resistance in the middle of the balloon in this case, allowing the middle to expand first. This same concept can be applied to control inflation in the directions distal to proximal, proximal to distal, or ends to middle simply by varying the layers comprising the cover accordingly such that fewer layers are used where preferential inflation is desired.

In another embodiment, control of the balloon expansion profile can be achieved by preconditioning a portion of the balloon. Preconditioning can occur via repeated blow molding in different sized molds or can occur via one or more partial or full inflations of a portion of the balloon. Preconditioned regions of the balloon preferentially inflate before non-preconditioned regions since preconditioning lessens the force required to initiate an increase in diameter. Constraints (for example, rigid metal rings) can be used as manufacturing aids to inhibit inflation preconditioning in selected regions of the balloon.

Said drug delivery construct can be configured such that control of the balloon expansion profile can be independent of the final (nominal) diameter of the balloon. In one embodiment, the structural layer can be constructed such that although portions of the balloon may inflate in varying sequences, all regions of the balloon will ultimately reach the same final diameter. For example, a drug delivery construct with a middle out inflation profile can be designed such that the middle portion of the balloon begins to inflate at two atmospheres of pressure. The ends of the same drug delivery construct can be designed to increase in diameter at four atmospheres of pressure. At eight atmospheres, the balloon can be constructed such that the balloon ends reach a diameter essentially equal to the diameter of the middle. At such an inflation pressure, the balloon has essentially an equal diameter along its length. This can be achieved for example, by controlling the expansion profile via the structural layer, but using the underlying balloon to control the final diameter at full inflation.

The agent delivery construct of the invention comprises a structural layer and/or the expandable member that comprises a coating (that may or may not comprise at least one therapeutic agent) on said surface of said structural layer and/or the expandable member. Said coating can render said agent delivery construct very rigid. Due to its rigidity said agent delivery construct may be difficult to track through tortuous anatomy. Thus, in one embodiment, after applying coating to said structural layer and/or expandable member, the outer sheath is slipped over said structural layer and/or expandable member and then the coating is cracked by pre-stressing, such as through inflating, bending and/or twisting said structural layer and/or the expandable member-outer sheath construct. The coating substrate, e.g., the structural layer, can be engineered to facilitate cracking by providing a rough surface or a surface that helps to concentrate stress in localized areas of the coating such as a cover with small nondistensible regions or areas of higher distention. This allows said agent delivery construct to be more conformable, while not allowing any particulates to escape the outer-sheath prior to treatment. In another embodiment, instead of fully coating the structural layer and/or the expandable member, said coating is applied as "rings" of coating such that in between said "rings" of coatings the structural layer and/or the expandable member is conformable and allow said structural layer and/or expandable member to bend at the uncoated region (allows for flexing). Said rings may also reduce hydration time of the coating by maximizing surface area of the coating in contact with a hydrating fluid. Reduced hydration time can improve overall system performance (e.g., time to effect delivery, degree of drug uptake, etc.). In another embodiment, rather than "rings", the coating and/or therapeutic agent are applied to the structural layer and/or the expandable member as an extruded, helically laid-down, continuous beading. In another embodiment, rather than "rings", the coating and/or therapeutic agent are applied to the structural layer and/or the expandable member as discrete dots or other shapes or discrete patterns. In another embodiment, said rings of coating can comprise the same therapeutic agent and/or different therapeutic agent and/or different coatings.

In another embodiment, the coating and/or therapeutic agent are applied to the structural layer and/or the expandable member in a discontinuous fashion. For example, the amount or thickness of coating may be varied over the surface of the substrate. In instances where drug delivery is desired only at the proximal and distal ends of a stent, for example, coatings applied to only the proximal and distal portions of the structural layer, expandable member and/or outer sheath (leaving the middle portion uncoated) may be desirable, especially for treatment or prevention of stent end stenosis. Coating and/or therapeutic agent compounds may similarly vary in thickness and/or over the area of the structural layer and/or the expandable member.

In another embodiment, the viscosity of the coating and/or therapeutic agent can be modified to improve the dwell time of the agent to the treatment site. In an embodiment, coating can comprise a thickening agent, e.g. a gelling agent.

In another embodiment, said agent delivery construct comprises an underlying medical balloon, a structural layer (optional), a coating comprising a therapeutic agent, and outer sheath wherein said components are mounted on a catheter. In one embodiment, the expanded diameter of said balloon is about 1 mm, about 2 mm, about 4 mm, about 5 mm, about 6 mm, about 7 mm, about 8 mm, about 9 mm, or about 10 mm in diameter with lengths ranging from about 30 to about 150 mm. In another embodiment, said balloon catheter will range in length from about 90 to about 150 cm. In another embodiment, said delivery balloon of the invention is about 5, 6, 7, 8, 9 or 10 French (Fr) in size before introduction into a body vessel, cavity or duct.

In another embodiment, said agent delivery construct comprises an underlying medical balloon, a structural layer (optional), a coating comprising a therapeutic agent, and outer sheath wherein said components are mounted on a catheter but may be detached from the catheter for short or long term implantation.

According to the present invention, said balloon may be formed using any materials known to those of skill in the art. Commonly employed materials include the thermoplastic elastomeric and non-elastomeric polymers and the thermosets.

Examples of suitable materials include but are not limited to, polyolefins, polyesters, polyurethanes, polyamides, polyether block amides, polyimides, polycarbonates, polyphenylene sulfides, polyphenylene oxides, polyethers, silicones, polycarbonates, styrenic polymers, copolymers thereof, and mixtures thereof. Some of these classes are available both as thermosets and as thermoplastic polymers. See, U.S. Pat. No. 5,500,181, for example. As used herein, the term "copolymer" shall be used to refer to any polymer formed from two or more monomers, e.g. 2, 3, 4, 5 and so on and so forth.

Useful polyamides include, but are not limited to, nylon 12, nylon 11, nylon 9, nylon 6/9 and nylon 6/6. The use of such materials is described in U.S. Pat. No. 4,906,244, for example.

Examples of some copolymers of such materials include the polyether-block-amides, available from Elf Atochem North America in Philadelphia, Pa. under the tradename of PEBAX®. Another suitable copolymer is a polyetheresteramide.

Suitable polyester copolymers, include, for example, polyethyelene terephthalate and polybutylene terephthalate, polyester ethers and polyester elastomer copolymers such as those available from DuPont in Wilmington, Del. under the tradename of HYTREL®.

Block copolymer elastomers such as those copolymers having styrene end blocks, and midblocks formed from butadiene, isoprene, ethylene/butylene, ethylene/propene, and so forth may be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether may also be employed herein.

Specific examples of polyester/polyether block copolymers are poly(butylene terephthalate)-block-poly(tetramethylene oxide) polymers such as ARNITEL® EM 740, available from DSM Engineering Plastics and HYTREL® polymers available from DuPont de Nemours & Co, already mentioned above.

Suitable materials which can be employed in balloon formation are further described in, for example, U.S. Pat. No. 6,406,457; U.S. Pat. No. 6,284,333; U.S. Pat. No. 6,171,278; U.S. Pat. No. 6,146,356; U.S. Pat. No. 5,951,941; U.S. Pat. No. 5,830,182; U.S. Pat. No. 5,556,383; U.S. Pat. No. 5,447,497; U.S. Pat. No. 5,403,340; U.S. Pat. No. 5,348,538; and U.S. Pat. No. 5,330,428.

The above materials are intended for illustrative purposes only, and not as a limitation on the scope of the present invention. Suitable polymeric materials available for use are vast and too numerous to be listed herein and are known to those of ordinary skill in the art.

Balloon formation may be carried out in any conventional manner using known extrusion, blow molding and other molding techniques. Typically, there are three major steps in the process which include extruding a tubular preform, molding the balloon and annealing the balloon. Depending on the balloon material employed, the preform may be axially stretched before it is blown. Techniques for balloon formation are described in U.S. Pat. No. 4,490,421, RE32, 983, RE33,561 and U.S. Pat. No. 5,348,538.

The balloon may be attached to the tubular body by various bonding means known to the skilled artisan. Examples include, but are not limited to, solvent bonding, laser welding, thermal adhesive bonding and heat shrinking or sealing. The selection of the bonding technique is dependent upon the materials from which the expandable element and tubular body are prepared. Refer to U.S. Pat. No. 7,048,713 to Wang for general teachings relating to the bonding of a balloon to a catheter.

In another embodiment, rather than a balloon acting as the expansion element for embodiments of the present invention, other expandable devices may be used. For example, a swellable gel tube can be located surrounding a catheter. A coating and/or therapeutic agent can then be applied to the outer surface of the gel tube. Optionally, a structural cover can be located between the gel tube and the coating and/or therapeutic agent. An outer sheath is then applied over the construct and sealingly attached to the catheter. A system is provided for hydrating the gel tube at the appropriate time during treatment. Upon hydration, the gel tube expands in diameter and drives the hydrated coating and/or therapeutic agent into contact with the tissue to be treated. In another embodiment, hydration of the gel tube also hydrates (or assists the hydration of) the coating and/or therapeutic agent.

The agent delivery constructs provided by the present invention are suitable for a wide range of applications including, for example, a range of medical treatment applications within the body. Exemplary applications include use as a catheter balloon for transferred drug to or placement or "touch-up" of implanted vascular grafts, stents, stent-grafts, a permanent or temporary prosthesis, or other type of medical implant, treating a targeted tissue within the body, and treating any body cavity, space, or hollow organ passage (s) such as blood vessels, the urinary tract, the intestinal tract, nasal cavity, neural sheath, intervertebral regions, bone cavities, esophagus, intrauterine spaces, pancreatic and bile ducts, rectum, and those previously intervened body spaces that have implanted vascular grafts, stents, prosthesis, or other type of medical implants. Additional examples include an agent delivery construct device for the removal of obstructions such as emboli and thrombi from blood vessels, as a dilation device to restore patency to an occluded body passage, as an occlusion device to selectively deliver a means to obstruct or fill a passage or space, and as a centering mechanism for transluminal instruments like catheters. In one embodiment, agent delivery constructs provided by the present invention can be used to treat stent restenosis or treat tissue sites where previously placed drug delivery constructs have failed. In another embodiment, agent delivery constructs as described herein can be used to establish or maintain arteriovenous access sites, e.g., those used during kidney dialysis. In one embodiment, said agent delivery construct comprises a medical balloon used for Percutaneous Transluminal Angioplasty (PTA) in patients with obstructive disease of the peripheral arteries. In another embodiment, agent delivery constructs provided by the present invention can be used to treat coronary stenosis or obstructions.

Another embodiment of the invention comprises a balloon catheter comprising, a balloon comprising a coating and a therapeutic agent disposed around the outer surface of said balloon, a sheath disposed around said balloon wherein said sheath has a microstructure composed of nodes interconnected by fibrils that allows microscopic or macroscopic wetting of said sheath in the unexpanded state, wherein said coating and therapeutic agent are disposed between the surface of the balloon and the sheath. Said sheath is retractable. In an embodiment, the outer sheath is a substantial barrier to the transfer of therapeutic agent through the sheath prior to expansion. In another embodiment, said coating remains substantially adhered to the target tissue for greater than 1 minute after balloon deflation. In another embodiment, said sheath contains the wetting agent polyvinyl alcohol to facilitate wetting of the sheath. In another embodiment, said sheath comprises a fluoropolymer. In another embodiment, said sheath comprises ePTFE. In another embodiment, said coating comprises a hydrophilic component. In another embodiment, said coating comprises at least one hydrophilic component selected from the group consisting of benzethonium chloride, PEG, poloxamer, sodium salicylate, and hydroxypropyl-β-cyclodextrin. In another embodiment, said therapeutic agent is a hydrophilic agent. In another embodiment, said therapeutic agent is a hydrophobic agent. In another embodiment, said hydrophobic agent is selected from the group consisting of taxane domain-binding drugs, such as paclitaxel, and rapamycin. In another embodiment, said balloon further comprises a structural layer. In another embodiment, said structural layer comprises said coating and therapeutic agent. In another embodiment, the outer sheath retracts as said balloon expands.

Other embodiments of the invention comprise a method of delivering a therapeutic agent to a desired location within a vessel comprising, inserting a catheter in a vessel, said catheter comprising an expandable member comprising a coating with a therapeutic agent, a sheath disposed around said expandable member, wherein said sheath has a selectively permeable microstructure that limits and restricts bulk transfer of said coating from being transported through said sheath but allows said coating to be at least partially hydrated, and wherein said coating and therapeutic agent are disposed interior to the sheath's outermost layer (or between the surface of the expandable member and the sheath), advancing said catheter to a desired location within said vessel, and expanding the expandable member at the desired location within said vessel, and wherein said sheath retracts and exposes a hydrated or partially hydrated coating. In one embodiment, said expandable member is a medical balloon. In another embodiment, said sheath comprises a fluoropolymer. In another embodiment, the sheath comprises a microstructure comprised of nodes interconnected by fibrils. In another embodiment, said sheath comprises ePTFE. In another embodiment, said therapeutic agent is a hydrophilic agent. In another embodiment, said therapeutic agent is a hydrophobic agent. In another embodiment, said therapeutic agent is paclitaxel. In another embodiment, said coating is hydrophilic. In another embodiment, said expandable member further comprises a structural layer. In another embodiment, said structural layer comprises said coating and therapeutic agent. In another embodiment, the hydrated or partially hydrated hydrophilic coating containing a therapeutic agent is tissue adherent, and thus, even after the expandable member is removed from the site, the drug continues to be absorbed into the tissue until the coating and drug dissipate from the site. This approach effectively increases the total drug delivery time to the tissue.

In another embodiment of the invention, agent delivery constructs of the invention can be applied in configurations other than those which are radially circular. For example, this invention can be used in conjunction with planar devices such as wound dressings, implantable patches (including vascular and hernia patches), transdermal patches, filters, various device delivery components, occluders, and orthopedic implants. In one embodiment, the system of the invention may be incorporated into an implantable lead (e.g., a cardiac or neurostimulation lead), provided the lead is compatible with an expandable member, e.g., features a lumen or pocket into which an expandable member is positionable.

Other embodiments of the invention comprise a hydrophilic coating comprising at least one therapeutic agent applied to at least a portion of the exterior surface of an expandable catheter stent, stent-graft, or blood vessel graft over which is placed an outer sheath with a selectively permeable microstructure. During delivery or when the expandable catheter, stent, stent-graft, or blood vessel graft is exposed to a body fluid, microwetting of the coating occurs. Upon expansion of the catheter, stent, stent-graft or graft, the outer sheath disposed over the expandable device retracts to expose a hydrated or partially hydrated coating. In an embodiment, the coating can be located on the proximal and distal sections of the expandable catheter, stent, stent-graft, or blood vessel graft, e.g., to help decrease the incidence of or prevent edge restenosis.

In another embodiment, the expandable medical device of the invention is combined with an occlusion device such as a balloon located proximate the device. Said occlusion device may mitigate the movement of drug far from the treatment site. In one embodiment, the bodily fluids isolated by this system may be withdrawn from the body by aspiration prior to removal of the system.

It is contemplated that a plurality of described embodiments can be attached to a single catheter to facilitate a plurality of drug delivery events or dosages can be delivered with the use of a single device. In the case of a balloon embodiment, a catheter can comprise discrete inflation lumens for each balloon, or some other mechanism for limiting and controlling the inflation to a particular balloon.

Optionally, described embodiments can be configured to apply therapeutic vibrational energy, radiofrequency energy, or the like to enhance drug delivery. Similarly, iontophoresis can be used to aid in the transfer of the therapeutic agent across the outer sheath and into surrounding tissue. In various embodiments, the pressure levels within the expandable member can be pulsed to create multiple, increased pressure events, which can facilitate transfer of the therapeutic agent and/or create multiple drug delivery events.

Another embodiment of the invention comprises a kit comprising a structural layer comprising a dehydrated or partially dehydrated coating (further comprising a therapeutic agent) and an outer sheath over said structural layer. Such a kit can convert an off the shelf balloon catheter or catheter into an agent delivery construct of the invention. In another embodiment, said kit comprises an adhesive (including tapes and liquid adhesives) for bonding said structural layer and outer sheath to a balloon catheter. In another embodiment, said structural layer, outer sheath and adhesive are sterile, placed in a container with an instruction pamphlet explaining how to apply said structural layer and outer sheath onto said balloon catheter. In another embodiment, said balloon catheter is also sterile.

Another embodiment of the invention comprises a PTA or PTCA balloon catheter sheath that extends along a substantial length of the catheter. The sheath at a distal portion comprises a structural layer, drug coating, and an outer sheath about the PTA or PTCA balloon catheter sheath at the location of the PTA or PTCA balloon.

Another embodiment the invention comprises a medical device comprising a mass transport barrier and a solubilized therapeutic agent, wherein said mass transport barrier has a first configuration that is substantially permeable to bodily fluids and impermeable to the solubilized therapeutic agent. In one embodiment, said a mass transport barrier is treated with a wetting agent, as described above.

Another embodiment the invention comprises a method of delivering a bioactive agent to biological target through a mass transport barrier, said method comprising a mass transport barrier and a solubilized therapeutic agent, wherein said mass transport barrier has a first configuration that is substantially permeable to bodily fluids and impermeable to the solubilized therapeutic agent, wherein upon of an application of mechanical force to the mass transport barrier, at least a portion of said barrier is retracted, thereby allowing delivery of the solubilized therapeutic agent. In one embodiment, said a mass transport barrier is treated with a wetting agent, as described above.

Figure 9A:
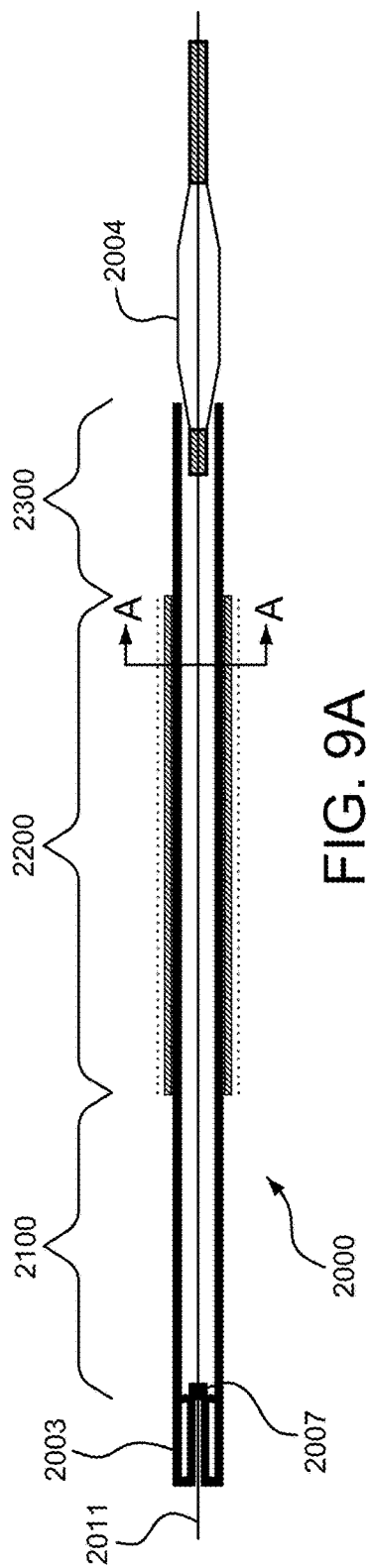
FIGS. 9A to 9B illustrate a drug delivery embodiment of the present disclosure comprising a catheter that can be tracked to a targeted area and also be expanded by an expandable device, such as a medical balloon.
Figure 9B:
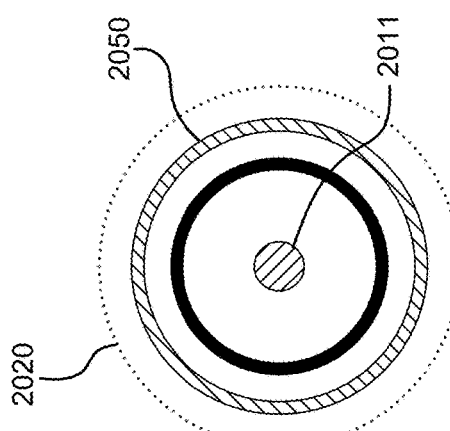

Due to the toxicity of some of the drugs delivered, it is important to deliver therapeutic agents to a specific target. In addition, if several areas are to be targeted for therapeutic agent delivery, the problem of overlapping treatment (i.e., areas that may get several doses of a therapeutic agent) and the need to swap multiple drug delivery balloon catheters can be of major concern. One way to overcome these deficiencies is shown in FIGS. 9A and 9B. FIG. 9A illustrates a catheter that can be tracked to a targeted area and also be expanded by an expandable device, such as a medical balloon. Catheter 2000 comprises tip 2003 that interfaces with guidewire 2011. Guidewire 2011 may further comprise guidewire stop 2007. Guidewire stop 2007 can engage with tip 2003 and allow the catheter to be tensioned for better balloon tracking. Catheter 2000 further comprises uncoated section 2100, a coated section 2200, and a stiffer tube section 2300. FIG. 9A further depicts a balloon catheter with a balloon 2004 at the distal end of said balloon catheter. Said balloon catheter with balloon 2004 can be placed inside said catheter 2000. Stiffer tube section 2300 allows for said balloon catheter to be more easily inserted into catheter 2000.

FIG. 9B depicts a cross section at line A-A of coated section 2200. FIG. 5B depicts a distensible layer 2040 (similar to the structural layer described above), a coating (comprising a therapeutic agent) 2050, outer sheath 2020 and guidewire 2011.

Figure 10A:
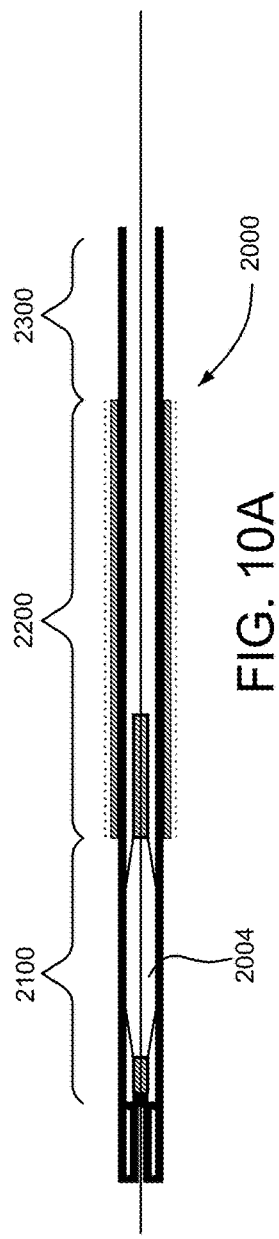
Figure 10B:
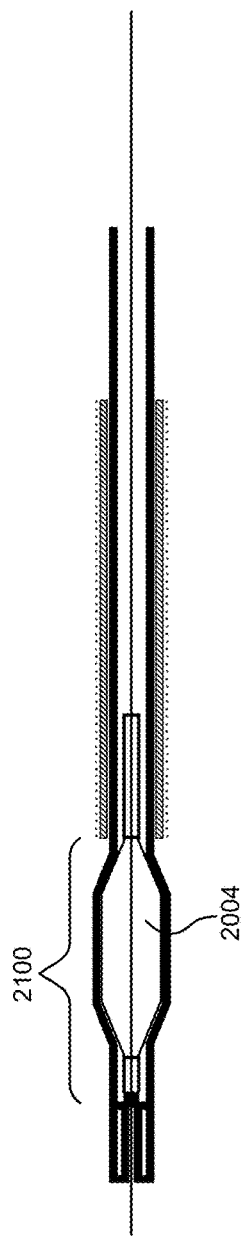

FIGS. 10A through 10D depict the procedural steps for one method of use employing this embodiment. Catheter 2000 is tracked and placed in a targeted vessel for treatment. Then balloon 2004 is tracked into catheter 2000 to a desired location within catheter 2000, as depicted in FIG. 10A. In one embodiment, balloon 2004 is tracked and inflated in uncoated section 2100 to deliver a standard Percutaneous Transluminal Angioplasty (PTA) treatment, as depicted in FIG. 10B. Then, balloon 2004 is deflated after PTA, catheter 2000 is advanced distally to position coated section 2200 at the PTA site and balloon 2004 is repositioned under coated section 2200, as depicted in FIG. 10C. Then, balloon is inflated in coated section 2200, as depicting in FIG. 10D. This can facilitate retraction of the sheath and delivery of a therapeutic agent and/or coating to the vessel. In another embodiment, said balloon is deflated and the outer sheath moves back to its unretracted state. Said balloon is repositioned to another area, and the balloon can be reinflated to deliver another dose of a therapeutic agent. In another embodiment, to aid visualization by the clinician, radiopaque or other imaging markers are incorporated in catheter 2000 and/or balloon catheter 2004. In another embodiment, several doses can be delivered to different areas in a vessel by repositioning balloon 2004 and/or catheter 2000. The mechanisms by which the catheter is made, the coating and therapeutic agent are loaded and delivered are described above. In another embodiment, said catheter comprises an elastomeric element (as described above) so that after balloon inflation catheter 2000 can recompact to or near to its delivery diameter.

Thus, one embodiment of the invention comprises a system of delivering a therapeutic agent comprising, a catheter comprising a distensible layer, a coating comprising a therapeutic agent disposed around said distensible layer, and an outer sheath over said distensible layer and said coating; wherein said outer sheath has a permeable microstructure that substantially prevents distension transfer of therapeutic agent through said outer sheath, a medical balloon catheter, wherein said medical balloon is on the distal end of a catheter; wherein said medical balloon can be placed with said catheter; and wherein when said medical balloon is inflated in said catheter, it will distend said distensible layer and retract the outer sheath allowing delivery of said coating and therapeutic agent to an area external to said outer sheath. In another embodiment, said sheath undergoes microscopic or macroscopic wetting in a vessel while said balloon and sheath are in the unexpanded state and being delivered to a desired location within a vessel. In another embodiment, said sheath comprises a wetting agent and will wet out completely when in contact with fluid in a first diameter. In another embodiment, said coating hydrates when said outer sheath is in a first diameter. In another embodiment, said outer sheath comprises a fluoropolymer. In another embodiment, said outer sheath comprises ePTFE. In another embodiment, said hydrophobic agent is selected from the group consisting of taxane domain-binding drugs, such as paclitaxel, and rapamycin. In another embodiment, said coating comprises at least one hydrophilic component selected from the group consisting of benzethonium chloride, PEG, poloxamer, sodium salicylate, and hydroxypropyl-β-cyclodextrin.

While particular embodiments of the present invention have been illustrated and described herein, the present invention should not be limited to such illustrations and descriptions. It should be apparent that changes and modifications may be incorporated and embodied as part of the present invention within the scope of the following claims. The following examples are further offered to illustrate the present invention.

EXAMPLES

Example 1: Preparation of a Structural Cover

A structural cover was prepared using methods as essentially taught in U.S. Pat. No. 6,120,477 (Campbell, et al.). A film tube was made by helically wrapping 20 layers of a highly fibrillated 5 micron thick ePTFE film (U.S. Pat. No. 5,476,589 to Bacino) at an 83.4° angle to the tubular axis on a 7 mm stainless steel mandrel. Ten layers of the ePTFE were wrapped in one direction and ten layers were wrapped in the opposing direction. The mandrel was baked in an oven set at 380° C. for 6 minutes to fuse the layers together. The resulting tube was removed from the mandrel and "necked" (stretched) down to a diameter below 2.2 mm. This necked tube was placed onto a 2.2 mm stainless steel mandrel and overwrapped with approximately 5 layers of a sacrificial ePTFE film to prevent the tube from wrinkling in the subsequent steps. Next, the tube construct was uniformly compressed to approximately 65% of its original length. The construct was placed in an oven set at the 380° C. for 1 minute and then the sacrificial ePTFE layer was removed. This construct was removed from the mandrel and cut to a 65.0 mm length. In alternate embodiments, this structural layer may comprise an elastomer to aid in recompaction of the underlying balloon (see, e.g., U.S. Pat. No. 6,120,477, Campbell, et al.).

Example 2: Assembly of a Structural Cover onto a Balloon Catheter

A semicompliant balloon catheter was purchased from Bavaria Medizin Technologie, Oberpfaffenhofen, Germany (model # BMT-035, article#08PL-604A, with balloon dimensions of 6.0 mm×40 mm). The balloon has the following specifications: a nylon balloon with a 6 atmosphere (atm) nominal inflation pressure and a 14 atm rated burst pressure, a 6 mm nominal diameter, 40 mm balloon working length, mounted on a 0.9 mm guidewire compatible catheter.

The structural tube, as described in Example 1, was centered over the semicompliant balloon and the ends were wetted with a Loctite 7701 primer (Henkel AG & Co. KgaA, Düsseldorf, Germany). The ends were then fixedly attached to the catheter using five layers of a 6.4 mm width of ePTFE film which were wrapped circumferentially around the balloon ends while Loctite 4981 (Henkel AG & Co. KgaA, Düsseldorf, Germany) was applied to the film.

The structural cover was colored black using a Sharpie® permanent marker (Sanford Corporation, Oak Brook, Ill.). The coloring of the structural cover was used to show the extent of outer sheath wetting, as described in more detail below. The structural tube is also known herein as the "structural cover", especially when it is placed and secured over a balloon.

Example 3: Application of a Hydrophilic Coating to a Structural Cover

A 5% (by weight) aqueous solution of polyvinyl alcohol (PVA, USP grade, Spectrum Chemicals & Laboratory Products, Gardena, Calif.) was prepared. This solution is referred herein as Solution 3. A structural tube was assembled onto a balloon catheter as described in Example 2, and was dip-coated with Solution 3 for 30 seconds while rotating. After the 30 seconds, the device was removed from Solution 3. While rotating the device, a heat gun was used to blow warm air (of about 40° C.) over the device for approximately 3 minutes. This process was then repeated two additional times. Next, the device was placed into an oven set at 60° C. for approximately 10 minutes.

The resulting coated structure had an outer diameter (OD) of less than 3.2 mm.

Example 4: Preparation of an Outer Sheath Comprising a Neckable Element

Figure 11A:
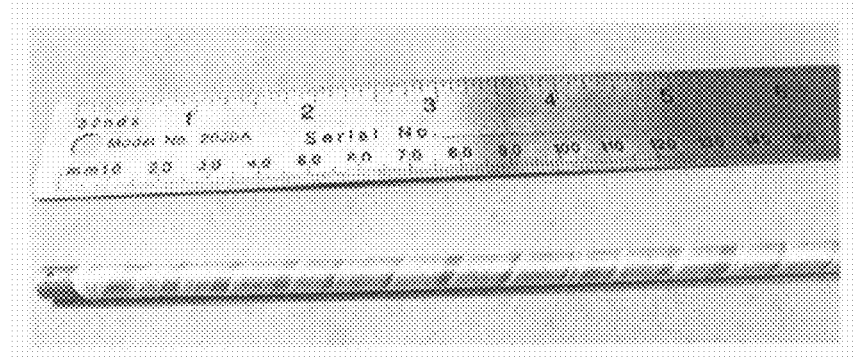
FIGS. 11A through 11C depict the stages of making an agent delivery construct comprising a neckable element helically wrapped around an expandable member.
Figure 11B:
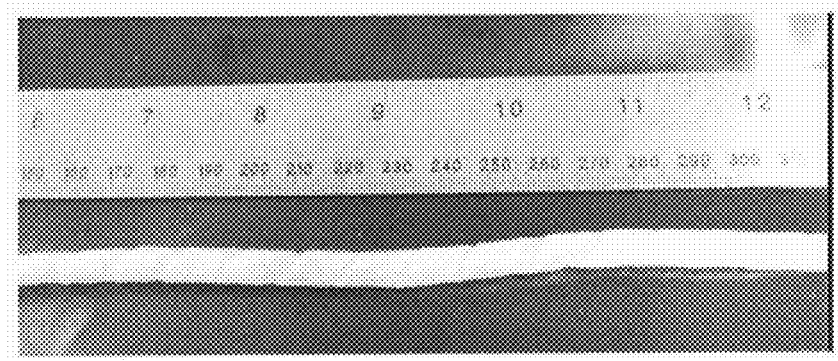
Figure 11C:
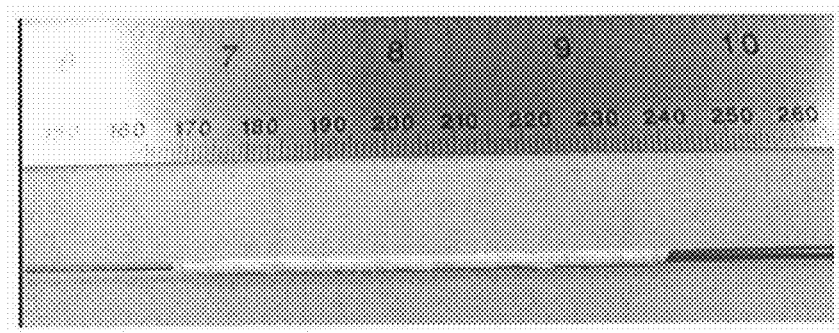

An outer sheath layer was prepared using the following method. As depicted in FIG. 11A, a film tube was created by helically wrapping at least one pass with 50% overlap of a thin ePTFE film (as described in U.S. Pat. No. 5,814,405 Branca et al.) at a ~45° angle to the tubular axis on a 6 mm stainless steel mandrel. The mandrel comprising the ePTFE layers was baked in an oven set at 380° C. for 3 minutes to fuse the layers together. The resulting tube was removed from the mandrel, as depicted in FIG. 11B. After removal from the mandrel, flattened and helically wrapped around a balloon, structural layer, and a coating to form the outer sheath layer, attached at distal and proximal ends of balloon and excess length was trimmed away. Specifically, the bonded areas were wetted with a Loctite 7701 primer (Henkel AG & Co. KgaA, Düsseldorf, Germany). The ends of the outer sheath layer were then fixedly attached to the balloon using five layers of a 6.4 mm width of ePTFE film. Specifically, the ePTFE film layers were wrapped circumferentially around the balloon ends while Loctite 4981 (Henkel AG & Co. KgaA, Düsseldorf, Germany) was applied to the film. The drug delivery balloon is depicted in FIG. 11C in its unexpanded state.

Numerous characteristics and advantages of the present invention have been set forth in the preceding description, including preferred and alternate embodiments together with details of the structure and function of the invention. The disclosure is intended as illustrative only and as such is not intended to be exhaustive. It will be evident to those skilled in the art that various modifications may be made, especially in matters of structure, materials, elements, components, shape, size and arrangement of parts within the principals of the invention, to the full extent indicated by the broad, general meaning of the terms in which the appended claims are expressed. To the extent that these various modifications do not depart from the spirit and scope of the appended claims, they are intended to be encompassed therein. In addition to being directed to the embodiments described above and claimed below, the present invention is further directed to embodiments having different combinations of the features described above and claimed below. As such, the invention is also directed to other embodiments having any other possible combination of the dependent features claimed below.

What is claimed is:

1. A medical device comprising:
    an inflation port in fluid communication with a lumen of an expandable member, the expandable member having an uninflated diameter and being configured to expand to an inflated diameter;
    a coating comprising a therapeutic agent disposed on the expandable member, wherein the therapeutic agent is complexed or sequestered by one or more solubilizing agents; and
    a retractable outer sheath having a permeable microstructure comprising micropores, the retractable outer sheath disposed around the expandable member and over the coating;
    wherein when the expandable member is exposed to a fluid while the expandable member is at the uninflated diameter, the micropores are configured to permit at least partial replacement of air within the micropores with the fluid so as to allow for the fluid to pass through the retractable outer sheath and hydrate the coating so as to form solubilized particles of the therapeutic agent, and restrict release of the solubilized particles through the retractable outer sheath to limit unintended transfer of the therapeutic agent, and
    wherein inflation of the expandable member causes expansion of the micropores and exposes at least a portion of the hydrated coating, releasing the solubilized particles through the micropores.

2. The medical device of claim 1, wherein the retractable outer sheath comprises at least one of a dilatable slit or dilatable pore configured to dilate upon inflation of the expandable member.

3. The medical device of claim 1, wherein the retractable outer sheath comprises a frangible film configured to split open inflation of the expandable member.

4. The medical device of claim 1, wherein the retractable outer sheath comprises at least two adjacent film elements configured to separate upon inflation of the expandable member.

5. The medical device of claim 1, wherein the coating comprises a hydrophilic component.

6. The medical device of claim 5, wherein the hydrophilic component in the coating raises the solubility point of a hydrophobic therapeutic agent.

7. The medical device of claim 1, wherein the coating comprises at least one compound selected from the group consisting of benzethonium chloride, PEG, poloxamer, sodium salicylate, and hydroxypropyl-p-cyclodextrin.

8. The medical device of claim 1, wherein the therapeutic agent is a hydrophilic agent.

9. The medical device of claim 1, wherein the therapeutic agent is a hydrophobic agent.

10. The medical device of claim 9, wherein the hydrophobic agent is selected from the group consisting of taxane domain-binding drugs, such as paclitaxel, and rapamycin.

11. The medical device of claim 1, wherein the retractable outer sheath is treated with a wetting agent.

12. The medical device of claim 11, wherein the wetting agent is selected from the group consisting of heparin coatings, polyvinyl alcohol, polyethylene glycol, polypropylene glycol, dextran, agarose, alginate, polyacrylamide, polyglycidol, poly(vinyl alcohol-co-ethylene), poly(ethyleneglycol-co-propyleneglycol), poly(vinyl acetate-co-vinyl alcohol), poly(tetrafluoroethylene-co-vinyl alcohol), poly (acrylonitrile-co-acrylamide), poly(acrylonitrile-co-acrylic acid-co-acrylamidine), polyacrylic acid, poly-lysine, polyethyleneimine, polyvinyl pyrrolidone, polyhydroxyethylmethacrylate, and polysulfone, and their copolymers, either alone or in combination.

13. The medical device of claim 11, wherein the wetting agent is polyvinyl alcohol.

14. The medical device of claim 1, wherein the retractable outer sheath comprises a tetrafluoroethylene copolymer comprising a hydrophilic monomer.

15. The medical device of claim 1, wherein the retractable outer sheath comprises at least one material from the group consisting of a fluoropolymer, polyamides, polyurethane, polyolefins, polyesters, polyglycolic acid, poly lactic acid, and trimethylene carbonate.

16. The medical device of claim 1, wherein the retractable outer sheath comprises a fluoropolymer comprising the permeable microstructure.

17. The medical device of claim 1, wherein said the retractable outer sheath comprises ePTFE expanded polytetrafluoroethylene.

18. The medical device of claim 1, wherein the micropores restrict the release of particles greater than about 5 μm through the retractable outer sheath.

19. The medical device of claim 1, wherein the micropores restrict the release of particles greater than about 10 μm through the retractable outer sheath.

20. The medical device of claim 1, wherein the micropores restrict the release of particles greater than about 25 μm through the retractable outer sheath.

21. The medical device of claim 1, wherein the expandable member elastically expands to the inflated diameter.

22. A medical device comprising:
   an inflation port in fluid communication with a lumen of an expandable member, the expandable member having an uninflated diameter and being configured to expand to an inflated diameter;
   a coating comprising a therapeutic agent disposed on the expandable member, and
   a retractable outer sheath having a permeable microstructure comprising micropores, the retractable outer sheath disposed around the expandable member and over the coating;
   wherein when the expandable member is exposed to a fluid while the expandable member is at the uninflated diameter, the micropores are configured to permit at least partial replacement of air within the micropores with the fluid so as to allow for the fluid to pass through the retractable outer sheath and hydrate the coating so as to form solubilized particles of the therapeutic agent and restrict release of the solubilized particles through the retractable outer, and
   wherein when the expandable member is at a treatment site, the inflation port is configured to inflate and expand the expandable member to the inflated diameter, which causes the expansion of the micropores and exposes at least a portion of the hydrated coating, releasing the solubilized particles through the micropores.

* * * * *